United States Patent
Blin et al.

(10) Patent No.: US 8,119,110 B2
(45) Date of Patent: *Feb. 21, 2012

(54) COSMETIC COMPOSITION COMPRISING A BLOCK POLYMER AND A NON-VOLATILE SILICONE OIL

(75) Inventors: Xavier Blin, Paris (FR); Véronique Ferrari, Maisons-Alfort (FR)

(73) Assignee: L'Oreal S.A., Paris (FR)

( * ) Notice: Subject to any disclaimer, the term of this patent is extended or adjusted under 35 U.S.C. 154(b) by 2071 days.

This patent is subject to a terminal disclaimer.

(21) Appl. No.: 10/949,435

(22) Filed: Sep. 27, 2004

(65) Prior Publication Data

US 2005/0106197 A1 May 19, 2005

Related U.S. Application Data

(60) Provisional application No. 60/539,351, filed on Jan. 28, 2004.

(30) Foreign Application Priority Data

Sep. 26, 2003 (FR) ..................... 03 11337

(51) Int. Cl.
- A61K 8/72 (2006.01)
- C08F 265/02 (2006.01)
- C08F 265/06 (2006.01)

(52) U.S. Cl. ............... 424/70.11; 525/301; 525/242; 525/394; 525/308; 525/302; 526/307.6; 526/307.7; 526/328; 526/328.5

(58) Field of Classification Search .................. None
See application file for complete search history.

(56) References Cited

U.S. PATENT DOCUMENTS

| | | | |
|---|---|---|---|
| 2,047,398 A | 7/1936 | Voss et al. |
| 2,528,378 A | 10/1950 | Mannheimer et al. |
| 2,723,248 A | 11/1955 | Wright |
| 2,781,354 A | 2/1957 | Mannheimer et al. |
| 3,673,160 A | 6/1972 | Buisson et al. |
| 3,716,633 A | 2/1973 | Viout et al. |
| 3,802,841 A | 4/1974 | Robin |
| 3,836,537 A | 9/1974 | Boerwinkle et al. |
| 3,910,862 A | 10/1975 | Barabas et al. |
| 3,915,921 A | 10/1975 | Schlatzer et al. |
| 3,925,542 A | 12/1975 | Viout et al. |
| 3,937,811 A | 2/1976 | Papantoniou et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,030,512 A | 6/1977 | Papantoniou et al. |
| 4,031,307 A | 6/1977 | DeMartino et al. |
| 4,032,628 A | 6/1977 | Papantoniou et al. |
| 4,070,533 A | 1/1978 | Papantoniou et al. |
| 4,076,912 A | 2/1978 | Papantoniou et al. |
| RE29,871 E | 12/1978 | Papantoniou et al. |
| 4,128,631 A | 12/1978 | Lundmark et al. |
| 4,129,711 A | 12/1978 | Viout et al. |
| 4,131,576 A | 12/1978 | Iovine |
| 4,137,208 A | 1/1979 | Elliott |
| 4,152,416 A | 5/1979 | Spitzer et al. |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,425,326 A | 1/1984 | Guillon et al. |
| 4,509,949 A | 4/1985 | Huang et al. |
| 4,693,935 A | 9/1987 | Mazurek |
| 4,728,571 A | 3/1988 | Clemens et al. |
| 4,887,622 A | 12/1989 | Gueret |
| 4,972,037 A | 11/1990 | Garbe et al. |
| 4,981,902 A | 1/1991 | Mitra et al. |
| 4,981,903 A | 1/1991 | Garbe et al. |
| 5,000,937 A | 3/1991 | Grollier et al. |
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,219,945 A | 6/1993 | Dicker et al. |
| 5,266,321 A | 11/1993 | Shukuzaki |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,492,426 A | 2/1996 | Gueret |
| 5,492,466 A | 2/1996 | Gueret |

(Continued)

FOREIGN PATENT DOCUMENTS

DE 2 330 956 1/1974

(Continued)

OTHER PUBLICATIONS

Norjiri et al. Japan J. Appl. Phys 1971 803.*

(Continued)

Primary Examiner — Michael G Hartley
Assistant Examiner — Lance Wesley Rider
(74) Attorney, Agent, or Firm — Finnegan, Henderson, Farabow, Garrett & Dunner, LLP

(57) ABSTRACT

Disclosed herein are a cosmetic composition comprising a cosmetically acceptable organic liquid medium, at least one non-volatile silicone oil and at least one film-forming block ethylenic polymer and use of the composition for making up keratin materials, such as the skin.

127 Claims, No Drawings

U.S. PATENT DOCUMENTS

| | | |
|---|---|---|
| 5,519,063 A | 5/1996 | Mondet et al. |
| 5,538,717 A | 7/1996 | De La Poterie |
| 5,662,892 A * | 9/1997 | Bolich et al. ................. 424/70.1 |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,807,937 A * | 9/1998 | Matyjaszewski et al. .... 526/135 |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A * | 11/2000 | Anton et al. .................. 424/401 |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,254,878 B1 | 7/2001 | Bednarek et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 | 6/2002 | Galleguillos et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loeffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loeffler et al. |
| 7,399,478 B2 | 7/2008 | Loffler et al. |
| 7,803,877 B2 * | 9/2010 | Lion et al. ..................... 525/301 |
| 2001/0031269 A1 * | 10/2001 | Arnaud ........................ 424/401 |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 * | 6/2002 | Kantner et al. ............ 424/70.16 |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0153708 A1 | 8/2003 | Caneba et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |
| 2004/0096411 A1 | 5/2004 | Frechet et al. |
| 2004/0097657 A1 | 5/2004 | Morschhaeuser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhauser et al. |

| | | | |
|---|---|---|---|
| 2004/0120906 A1 | 6/2004 | Toumi et al. |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |
| 2005/0002724 A1 | 1/2005 | Blondeel et al. |
| 2005/0020779 A1 | 1/2005 | Mougin et al. |
| 2005/0032998 A1 | 2/2005 | Morschhauser et al. |
| 2005/0089536 A1 | 4/2005 | Loffler et al. |
| 2005/0095213 A1 | 5/2005 | Blin et al. |
| 2005/0106197 A1 | 5/2005 | Blin et al. |
| 2005/0129641 A1 | 6/2005 | Arnaud et al. |
| 2005/0201958 A1 | 9/2005 | De La Poterie |
| 2005/0220747 A1 | 10/2005 | Lion et al. |
| 2005/0232887 A1 | 10/2005 | Morschhauser et al. |
| 2005/0287103 A1 | 12/2005 | Filippi et al. |
| 2006/0093568 A1 | 5/2006 | Blin et al. |
| 2006/0099164 A1 | 5/2006 | De La Poterie et al. |
| 2006/0099231 A1 | 5/2006 | De La Poterie et al. |
| 2006/0115444 A1 | 6/2006 | Blin et al. |
| 2006/0127334 A1 | 6/2006 | Ferrari et al. |
| 2006/0134032 A1 | 6/2006 | Ilekti et al. |
| 2006/0134038 A1 | 6/2006 | De La Poterie et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2007/0003506 A1 | 1/2007 | Mougin et al. |
| 2007/0003507 A1 | 1/2007 | Mougin et al. |
| 2007/0166259 A1 | 7/2007 | Vicic et al. |
| 2008/0014232 A1 | 1/2008 | Arnaud et al. |
| 2008/0050329 A1 | 2/2008 | De La Poterie |
| 2008/0069793 A1 | 3/2008 | Loffler et al. |
| 2008/0107617 A1 | 5/2008 | Loffler et al. |
| 2008/0159965 A1 | 7/2008 | Mougin et al. |
| 2008/0207773 A1 | 8/2008 | Loffler et al. |
| 2008/0219943 A1 | 9/2008 | De La Poterie |

FOREIGN PATENT DOCUMENTS

| | | |
|---|---|---|
| DE | 100 22 247 | 11/2001 |
| DE | 100 29 697 | 12/2001 |
| EP | 1 279 398 | 9/1971 |
| EP | 0 080 976 | 6/1983 |
| EP | 0 295 886 | 12/1988 |
| EP | 0 320 218 | 6/1989 |
| EP | 0 173 109 | 10/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 216 479 | 8/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 815 836 | 1/1998 |
| EP | 0 847 752 | 6/1998 |
| EP | 0 861 859 | 9/1998 |
| EP | 0 951 897 | 10/1999 |
| EP | 1 018 311 A2 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 082 953 | 3/2001 |
| EP | 1 159 950 | 12/2001 |
| EP | 1 192 930 | 4/2002 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 | 4/2004 |
| EP | 0 955 039 | 5/2004 |
| EP | 1 421 928 | 5/2004 |
| EP | 1 440 680 | 7/2004 |
| EP | 1 518 534 | 3/2005 |
| EP | 1 518 535 | 3/2005 |
| EP | 1 604 634 | 12/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 140 977 | 1/1973 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 552 | 4/1995 |
| FR | 2 710 646 | 4/1995 |
| FR | 2 743 297 | 7/1997 |
| FR | 2 775 593 | 9/1999 |
| FR | 2 791 987 | 10/2000 |
| FR | 2 791 988 | 10/2000 |
| FR | 2 792 190 | 10/2000 |
| FR | 2 798 061 | 3/2001 |
| FR | 2 803 743 | 7/2001 |
| FR | 2 296 402 | 11/2001 |
| FR | 2 809 306 | 11/2001 |
| FR | 2 811 993 | 1/2002 |
| FR | 2 814 365 | 3/2002 |
| FR | 2 816 503 | 5/2002 |
| FR | 2 823 101 | 10/2002 |
| FR | 2 823 103 | 10/2002 |
| FR | 2 827 514 | 1/2003 |
| FR | 2 831 430 | 5/2003 |
| FR | 2 832 719 | 5/2003 |
| FR | 2 832 720 | 5/2003 |
| FR | 2 834 458 | 7/2003 |
| FR | 2 840 205 | 12/2003 |
| FR | 2 840 209 | 12/2003 |
| FR | 2 842 417 | 1/2004 |
| FR | 2 844 709 | 3/2004 |
| FR | 2 860 143 | 4/2005 |
| FR | 2 860 156 | 4/2005 |
| FR | 2 880 268 | 7/2006 |
| GB | 0 839 805 | 6/1960 |
| GB | 0 922 457 | 4/1963 |
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 5-221829 | 8/1993 |
| JP | 06-279323 | 10/1994 |
| JP | 07-196450 | 8/1995 |
| JP | 07-309721 | 11/1995 |
| JP | 07-324017 | 12/1995 |
| JP | 08-119836 | 5/1996 |
| JP | 09-263518 | 10/1997 |
| JP | 10-506404 | 6/1998 |
| JP | 11-100307 | 4/1999 |
| JP | 11-124312 | 5/1999 |
| JP | 2000-319325 | 11/2000 |
| JP | 2000-319326 | 11/2000 |
| JP | 2001-348553 | 12/2001 |
| JP | 2001-527559 | 12/2001 |
| JP | 2002-201110 | 7/2002 |
| JP | 2002-201244 | 7/2002 |
| JP | 2003-73222 | 3/2003 |

| | | |
|---|---|---|
| JP | 2003-081742 | 3/2003 |
| JP | 2003-286142 | 10/2003 |
| JP | 2004-002432 | 1/2004 |
| JP | 2004-002435 | 1/2004 |
| JP | 2004-149772 | 5/2004 |
| JP | 2004-269497 | 9/2004 |
| JP | 2005-104979 | 4/2005 |
| JP | 2006-503921 | 3/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/13863 | 3/2001 |
| WO | WO 01/19333 | 3/2001 |
| WO | WO 01/30886 | 5/2001 |
| WO | WO 01/43703 | 6/2001 |
| WO | WO 01/51018 | 7/2001 |
| WO | WO 01/95871 | 12/2001 |
| WO | WO 02/05762 | 1/2002 |
| WO | WO 02/05765 | 1/2002 |
| WO | WO 02/28358 | 4/2002 |
| WO | WO 02/34218 | 5/2002 |
| WO | WO 02/067877 | 9/2002 |
| WO | WO 02/080869 | 10/2002 |
| WO | WO 03/018423 A1 | 3/2003 |
| WO | WO 03/046032 A2 | 6/2003 |
| WO | WO 2004/022009 | 3/2004 |
| WO | WO 2004/022010 | 3/2004 |
| WO | WO 2004/024700 | 3/2004 |
| WO | WO 2004/028485 | 4/2004 |
| WO | WO 2004/028487 | 4/2004 |
| WO | WO 2004/028489 | 4/2004 |
| WO | WO 2004/028491 | 4/2004 |
| WO | WO 2005/030158 | 4/2005 |

OTHER PUBLICATIONS

Erichsen, abstract of MRS publiccation 2001.*
Cortazer et al., Polymer Bulletin 1, 149-154 (1987).*
English language abstract of FR 2 775 566 A1, Sep. 10, 1999.
English language abstract of JP 2003-40336, Feb. 13, 2003.
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/528,698, filed Mar. 22, 2005; Inventors: Veronique Ferrari et al.
Co-pending U.S. Appl. No. 10/528,699, filed Mar. 22, 2005; Inventors: Philippe Ilekti et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.
Co-pending U.S. Appl. No. 10/529,264, filed Mar. 25, 2005; Inventors: Veronique Ferrari et al.
Co-pending U.S. Appl. No. 10/529,265, filed Sep. 28, 2005; Inventors: Xavier Blin et al.
Co-pending U.S. Appl. No. 10/529,266, filed Mar. 25, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/529,318, filed Mar. 25, 2005; Inventors: Xavier Blin et al.
Co-pending U.S. Appl. No. 10/573,579; filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,388, filed Sep. 26, 2003; Inventors: Beatrice Toumi et al.
Co-pending U.S. Appl. No. 10/670,478, filed Sep. 26, 2003; Inventors: Bertrand Lion et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
English Derwent Abstract for EP 1 082 953, dated Mar. 14, 2001.
English Derwent Abstract for EP 1 159 950, dated Dec. 5, 2001.
English Derwent Abstract for FR 2 798 061, dated Mar. 9, 2001.
English Derwent Abstract for FR 2 803 743, dated Jul. 20, 2001.
English Derwent Abstract for FR 2 832 719, dated May 30, 2003.
English Derwent Abstract for WO 01/03538, dated Jan. 18, 2001.
English Derwent Abstract for WO 04/028489, dated Apr. 8, 2004.
English language Abstract of FR 2 710 552, dated Apr. 7, 1995.
English language Abstract of FR 2 834 458, dated Jul. 11, 2003.
English language Abstract of JP 07-309721, dated Nov. 28, 1995.
English language Abstract of JP 08-119836, dated May 14, 1996.
English language Abstract of WO 01/13863, dated Mar. 1, 2001.
English language Abstract of WO 01/51018, dated Jul. 19, 2001.
English language Derwent Abstract for EP 0 080 976, dated Jun. 8, 1983.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract of FR 2 140 977, dated Jan. 19, 1973.
English language Derwent Abstract of FR 2 860 156, Apr. 1, 2005.
English language Derwent Abstract of JP 11-100307, Apr. 13, 1999.
English language Derwent Abstract of JP 2001-348553, Dec. 18, 2001.
English language Derwent Abstract of JP 2002-201244, dated Jul. 19, 2002.
English language Derwent Abstract of JP 2004-002432, Jan. 8, 2004.
English language Derwent Abstract of JP 2004-002435, Jan. 8, 2004.
English language Derwent Abstract of JP 5-221829, dated Aug. 31, 1993.
European Search Report for EP 03 29 2383, dated May 17, 2004, in Co-pending U.S. Appl. No. 10/670,388.
Flick, "Cosmetic Additives: An Industrial Guide", Noyes Publications, Park Ridge, NJ, p. 266 (1991).
Fonnum, et al., Colloid Polym. Sci., 1993, 271: 380-389.
French Search Report for FR 02/11949 for Copending U.S. Appl. No. 10/670,478, dated Jul. 7, 2003.

French Search Report for FR 03/11340 for Copending U.S. Appl. No. 10/949,448, dated May 9, 2005.
French Search Report for FR 04/03090, dated Sep. 30, 2004.
French Search Report for FR 04/50572, for Copending U.S. Appl. No. 11/086,906, dated Nov. 9, 2004.
Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins", Journal of Paint Technology, vol. 39, No. 505, pp. 104-117 (1967).
HCAPLUS abstract 1964: 70247, abstracting: Develop. Ind. Microbiol., vol. 2, pp. 47-53 (1961).
International Search Report for PCT Application No. PCT/FR03/02849, dated Jun. 24, 2004.
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02841, dated Jun. 1, 2004.
International Search Report for PCT/FR03/02842 (Priority Application for U.S. Appl. No. 10/529,218), dated May 17, 2004.
International Search Report for PCT/FR03/02843 (Priority Application for U.S. Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. Appl. No. 10/528,835), dated May 17, 2004.
International Search Report for PCT/IB2005/000230, dated May 27, 2005.
International Search Report for PCT/IB2005/000236, dated Aug. 3, 2005.
Kirk-Othmer, "Encyclopedia of Chemical Technology", vol. 22, 3rd Edition, Wiley, 1979, pp. 333-432.
Nojima. S., "Melting Behavior of Poly (E-caprolactone)—block-polybutadiene Copolymers", Macromolecules, 32, 3727-3734 (1999).
Office Action mailed Aug. 12, 2005, in co-pending U.S. Appl. No. 10/670,478.
Office Action mailed Aug. 12, 2009 in co-pending U.S. Appl. No. 10/949,448.
Office Action mailed Aug. 18, 2009 in co-pending U.S. Appl. No. 10/529,264.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Dec. 29, 2009 in co-pending U.S. Appl. No. 10/529,265.
Office Action mailed Dec. 3, 2009 in co-pending U.S. Appl. No. 10/528,698.
Office Action mailed Jan. 7, 2008, in co-pending U.S. Appl. No. 10/670,388.
Office Action mailed Jun. 12, 2009 in co-pending U.S. Appl. No. 11/086,906.
Office Action mailed Jun. 24, 2009 in co-pending U.S. Appl. No. 10/528,698.
Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 26, 2008, in co-pending U.S. Appl. No. 10/670,478.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 17, 2009 in co-pending U.S. Appl. No. 10/528,835.
Office Action mailed Nov. 25, 2008, in co-pending U.S. Appl. No. 10/949,448.
Office Action mailed Nov. 25, 2008, in co-pending U.S. Appl. No. 10/670,388.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Oct. 27, 2009 in co-pending U.S. Appl. No. 10/529,218.
Office Action mailed Sep. 2, 2009 in co-pending U.S. Appl. No. 10/529,318.
Office Action mailed Sep. 28, 2009 in co-pending U.S. Appl. No. 10/670,478.
Office Action mailed Sep. 7, 2007, in co-pending U.S. Appl. No. 10/670,478.
Pigeon, R. et al., Chimie Macromoleculaire Appliquee, No. 600, 40/41 (1074), pp. 139-158.
Porter, "Chapter 7: Non Ionics," Handbook of Surfactants, 1991, pp. 116-178, Chapman and Hall, New York.
Prince, L.M. ed., Macroemulsions Theory and Practice, Academic Press (1977), pp. 21-32.
Rangarajan P., et al., "Morphology of Semi-Crystalline Block Copolymers of Ethylene—(ethylene-alt-propylene)," Macromolecules, 26, 4640-4645 (1993).
Richter, P. et al., "Polymer Aggregates with Crystalline Cores: The System Poly(ethylene)-poly(ethylene-propylene)," Macromolecules, 30, 1053-1068 (1997).
Thermal_Transisitons_of_Homopolymers.pdf. Thermal Transistions of Homopolymers: Glass Transistion & Melting Point Data. Accessed online Dec. 19, 2008 at: http://www.sigmaaldrich.com/etc/medialib/docs/Aldrich/General_Information/thermal_transitions_of_homopolymers.Par.0001.File.tmp/thermal_transitions_of_homopolymers.pdf.
Co-pending U.S. Appl. No. 11/878,067, filed Jul. 20, 2007; Inventors: Caroline Lebre et al.
Co-pending U.S. Appl. No. 11/878,849, filed Jul. 27, 2007; Inventors: Celine Farcet et al.
English language Abstract of EP 1 604 634, dated Dec. 14, 2005.
English language Abstract of FR 2 357 241, dated Feb. 3, 1978.
English language Abstract of FR 2 710 646, dated Apr. 7, 1995.
English language Abstract of FR 2 791 987, dated Oct. 13, 2000.
English language Abstract of FR 2 880 268, dated Jul. 7, 2006.
English language Abstract of JP 2006-151867, dated Jun. 15, 2006.
English language Derwent Abstract for JP 11-124312, dated May 11, 1999.
English language Derwent Abstract of DE 100 29 697, dated Dec. 20, 2001.
English language Derwent Abstract of EP 0 648 485, dated Apr. 19, 1995.
French Search Report for FR 04/03088, dated Nov. 2, 2004.
French Search Report for FR 06/53144, dated Feb. 13, 2007.
French Search Report for FR 06/53154, dated Apr. 2, 2007.
Notice of Allowance in U.S. Appl. No. 10/670,478, dated Jul. 6, 2010.
Office Action mailed Apr. 28, 2010, in co-pending U.S. Appl. No. 10/528,835.
Office Action mailed Aug. 31, 2010, in co-pending U.S. Appl. No. 10/529,265.
Office Action mailed Feb. 2, 2010, in co-pending U.S. Appl. No. 10/949,448.

Office Action mailed Feb. 27, 2009, in co-pending U.S. Appl. No. 11/878,849.
Office Action mailed Jan. 28, 2010, in co-pending U.S. Appl. No. 10/529,264.
Office Action mailed Jul. 12, 2010, in co-pending U.S. Appl. No. 11/858,994.
Office Action mailed Jul. 21, 2009, in co-pending U.S. Appl. No. 11/878,067.
Office Action mailed Jul. 28, 2010, in co-pending U.S. Appl. No. 10/529,264.
Office Action mailed Jul. 9, 2010, in co-pending U.S. Appl. No. 11/859,004.
Office Action mailed Jul. 9, 2010, in co-pending U.S. Appl. No. 11/859,015.
Office Action mailed Mar. 17, 2010, in co-pending U.S. Appl. No. 10/529,318.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed May 12, 2010, in co-pending U.S. Appl. No. 11/086,906.
Office Action mailed May 28, 2010, in co-pending U.S. Appl. No. 10/573,579.
Office Action mailed Sep. 9, 2009, in co-pending U.S. Appl. No. 11/878,849.
Related U.S. Appl. No. 11/089,172, filed Mar. 25, 2005, Inventors: Katarina Benabdillah et al.
Specific Gravity and Viscosity of Liquid Table; available at http://www.csgnetwork.com/sgvisc.html. Sesame seed oil information originally published Mar. 28, 2002.
Toniu, P. et al., "Process for Preparation of Block Polymers, Products Obtained by Means of the Process and Cosmetic Compositions Containing Them", 1973, French Patent Office, pp. 1-26 (English translation of French Patent No. FR2140977).
Notice of Allowance in U.S. Appl. No. 11/858,994, dated Nov. 26, 2010.
Notice of Allowance in U.S. Appl. No. 11/859,015 dated Jan. 6, 2011.
Office Action mailed Jan. 13, 2011, in co-pending U.S. Appl. No. 10/529,264.
Office Action mailed Jan. 13, 2011, in co-pending U.S. Appl. No. 10/529,267.
Office Action mailed Nov. 26, 2010, in co-pending U.S. Appl. No. 11/878,067.
English language Derwent Abstract of EP 1 366 746, Dec. 3, 2003.
English language Derwent Abstract of FR 2 832 720, May 30, 2003.

\* cited by examiner

COSMETIC COMPOSITION COMPRISING A BLOCK POLYMER AND A NON-VOLATILE SILICONE OIL

This application claims benefit of U.S. Provisional Application No. 60/539,351, filed Jan. 28, 2004.

The present disclosure relates to a cosmetic composition comprising at least one block polymer and at least one non-volatile silicone oil intended to be applied to human keratin materials, for instance the skin, the lips, the eyelashes, the eyebrows, the nails and the hair. In one embodiment, the composition is intended to be applied to the skin and the lips.

The composition according to the disclosure may be a makeup composition and/or a care composition for keratin materials, such as for the skin and the lips, and, for example, a makeup composition.

The makeup composition may be a lip makeup product (lipstick), a foundation, an eyeshadow, a makeup rouge, a concealer product, an eyeliner, a body makeup product, a mascara, a nail varnish or a hair makeup product.

The care composition may be a body and facial skin care product, such as an antisun product and a skin-coloring product (such as a self-tanning product). The composition may also be a haircare product, such as for holding the hairstyle and/or shaping the hair.

Lipstick and foundation compositions are commonly used to give the lips and the skin, such as the face, an aesthetic color. These makeup products generally contain fatty phases such as waxes and oils, pigments and/or fillers and optionally additives, for instance cosmetic and dermatological active agents.

When they are applied to the skin, these compositions may have the drawback of transferring, i.e., they may become at least partially deposited, and leave marks, on certain supports with which they may come into contact, such as a glass, a cup, a cigarette, an item of clothing or the skin. This may result in mediocre persistence of the applied film, making it necessary to regularly renew the application of the foundation or lipstick composition. Moreover, the appearance of these unacceptable marks, for example, on blouse collars, discourage certain consumers from using this type of makeup.

"Transfer-resistant" lip and skin makeup compositions are thus sought, which have the advantage of forming a deposit that may not become at least partially deposited onto the supports with which such compositions come into contact (glass, clothing, cigarette or fabric).

The known transfer-resistant compositions are generally based on silicone resins and volatile silicone oils, but these compositions may have the drawback of leaving on the skin and the lips, after evaporation of the volatile silicone oils, a deposit that may give the user a sensation of dryness and tautness: the makeup deposit may thus become uncomfortable over time. Furthermore, certain silicone resins may form a tacky makeup deposit and thus render the makeup even more uncomfortable.

To reduce the uncomfortable effect of the makeup, it is possible to add non-volatile hydrocarbon-based oils, for instance polyisobutylene, but it is then found that, by using only non-volatile hydrocarbon-based oils, the transfer-resistance property of the makeup may be altered.

Therefore, disclosed herein is a cosmetic composition that forms a deposit on keratin materials, such as on the skin and the lips, which can have good transfer-resistance properties and can be comfortable over time.

The present inventors have discovered that it is possible to obtain such a composition by using a particular block polymer combined with at least one non-volatile silicone oil present in a sufficient amount.

More specifically, disclosed herein is a cosmetic composition comprising at least one block polymer and a cosmetically acceptable organic liquid medium comprising a non-volatile liquid fatty phase, wherein:
the at least one block polymer is chosen from film-forming linear ethylenic polymers, and
the non-volatile liquid fatty phase comprises at least 30% by weight of at least one non-volatile silicone oil, relative to the total weight of the non-volatile liquid fatty phase.

In one embodiment, the at least one block polymer is free of styrene.

In another embodiment, the at least one block polymer is non-elastomeric.

In yet another embodiment, the at least one block polymer comprises at least one first block and at least one second block that have different glass transition temperatures (Tg), wherein the first and second blocks are connected together via an intermediate block comprising at least one constituent monomer of the first block and at least one constituent monomer of the second block.

The at least one block polymer has, for example, a polydispersity index I of greater than 2.

Further, for example, the first and second blocks are mutually incompatible.

The composition according to the disclosure makes it possible to obtain a deposit, such as a makeup deposit, on keratin materials, for example, on the skin and the lips, which can have good transfer-resistance properties, without any sensation of dryness, tautness or tack: the deposit thus obtained can therefore be comfortable for the user to wear over time.

Further disclosed herein is a process for making up keratin materials, such as the skin and the lips, comprising applying to the keratin materials, such as the skin and the lips, a composition as defined above.

Further disclosed herein is the use of the composition as defined above to obtain a deposit on keratin materials, such as on the skin and the lips, which has transfer-resistance properties and which is comfortable over time.

Even further disclosed herein is the use, in a cosmetic composition comprising a cosmetically acceptable organic liquid medium comprising a non-volatile liquid fatty phase:
of at least one film-forming linear block ethylenic polymer, and
of at least one non-volatile silicone oil present in an amount of at least 30% by weight, relative to the total weight of the non-volatile liquid fatty phase,
to obtain a deposit on keratin materials, such as on the skin and the lips, which has transfer-resistance properties and which is comfortable over time.

The term "cosmetically acceptable organic liquid medium" means a medium comprising at least one organic compound that is liquid at room temperature (25° C.) and atmospheric pressure ($10^5$ Pa) and that is compatible with keratin materials, for example, the skin and the lips, such as the organic solvents and oils commonly used in cosmetic compositions.

The at least one block polymer of the composition as disclosed herein is chosen from film-forming linear block ethylenic polymers.

The term "ethylenic polymer" means a polymer obtained by polymerization of monomers comprising at least one ethylenic unsaturation.

The term "block polymer" means a polymer comprising at least two different blocks such as at least three different blocks.

The polymer as disclosed herein is a polymer of linear structure. In contrast, a polymer of non-linear structure is, for example, a polymer of branched structure, of starburst or grafted form, or the like.

The term "film-forming polymer" means a polymer capable of forming, by itself or in the presence of a film-forming auxiliary agent, a continuous film that adheres to a support, such as to keratin materials.

In one embodiment, the composition according to the disclosure comprises at least one block polymer comprising at least one first block and at least one second block, which are, for example, mutually incompatible, and which have different glass transition temperatures (Tg), wherein the first and second blocks are connected together via an intermediate block comprising at least one constituent monomer of the first block and at least one constituent monomer of the second block.

It is pointed out that, as used herein, the terms "first" and "second" blocks do not in any way condition the order of the blocks in the structure of the polymer.

The term "at least one block" means one or more blocks.

The term "mutually incompatible blocks" means that the blend formed from the polymer corresponding to the first block and from the polymer corresponding to the second block is not miscible in the organic liquid that is of the majority amount by weight of the organic liquid medium of the composition, at room temperature (25° C.) and atmospheric pressure ($10^5$ Pa), for a polymer blend content of greater than or equal to 5% by weight, relative to the total weight of the blend (polymers and solvent), wherein:

i) the polymers corresponding to the first and second blocks are present in the blend in an amount such that the respective weight ratio ranges from 10:90 to 90:10, and ii) each of the polymers corresponding to the first and second blocks has an average (weight-average or number-average) molecular mass equal to that of the block polymer±15%.

In the case where the organic liquid medium comprises a mixture of organic liquids, and should two or more organic liquids be present in identical mass proportions, the polymer blend is immiscible in at least one of them.

Needless to say, in the case where the organic liquid medium comprises only one organic liquid, this liquid is the majority organic liquid.

In one embodiment, the majority organic liquid of the composition is the organic solvent for polymerization of the block polymer or the majority organic solvent of the mixture of organic solvents for polymerization of the block polymer.

The intermediate block is a block comprising at least one constituent monomer of the first block and at least one constituent monomer of the second block of the block polymer and makes it possible to "compatibilize" these blocks.

In one embodiment, the polymer used in the composition according to the disclosure does not comprise any silicon atoms in its skeleton. The term "skeleton" means the main chain of the polymer, as opposed to the pendent side chains.

In another embodiment, the polymer used in the composition according to the disclosure is not water-soluble, i.e., the polymer is not soluble in water or in a mixture of water and of linear or branched lower monoalcohols comprising from 2 to 5 carbon atoms, for instance ethanol, isopropanol and n-propanol, without pH modification, at an active material content of at least 1% by weight, at room temperature (25° C.).

The block polymer as disclosed herein is, for example, present in the organic liquid medium of the composition.

In one embodiment, the polymer used in the composition according to the disclosure is not an elastomer.

The term "non-elastomeric polymer" means a polymer which, when it is subjected to a constraint intended to stretch it (for example by 30% relative to its initial length), does not return to a length substantially identical to its initial length when the constraint ceases.

More specifically, the term "non-elastomeric polymer" means a polymer with an instantaneous recovery $R_i$<50% and a delayed recovery $R_{2h}$<70% after having been subjected to a 30% elongation. For example, $R_i$ is <30% and $R_{2h}$<50%.

More specifically, the non-elastomeric nature of the polymer is determined according to the following protocol:

A polymer film is prepared by pouring a solution of the polymer in a Teflon-coated mould, followed by drying for 7 days in an environment conditioned at 23±5° C. and 50±10% relative humidity.

A film about 100 µm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($l_0$) of the specimen.

The instantaneous recovery $R_i$ is determined in the following manner:

the specimen is pulled by 30% ($\epsilon_{max}$), i.e., about 0.3 times its initial length ($l_0$), the constraint is released by applying a return speed equal to the tensile speed, i.e., 50 mm/min, and the residual elongation of the specimen is measured as a percentage, after returning to zero constraint ($\epsilon_i$).

The percentage instantaneous recovery ($R_i$) is given by the following formula:

$$R_i = ((\epsilon_{max} - \epsilon_i)/\epsilon_{max}) \times 100$$

To determine the delayed recovery, the percentage residual elongation of the specimen ($\epsilon_{2h}$) is measured.

The percentage delayed recovery ($R_{2h}$) is given by the following formula:

$$R_{2h} = ((\epsilon_{max} - \epsilon_{2h})/\epsilon_{max}) \times 100$$

Purely as a guide, a polymer according to one embodiment as disclosed herein has an instantaneous recovery $R_i$ of 10% and a delayed recovery $R_{2h}$ of 30%.

For example, the block polymer used in the compositions according to the disclosure has a polydispersity index I of greater than 2.

The polydispersity index I of the polymer is equal to the ratio of the weight-average molecular weight (Mw) to the number-average molecular weight (Mn).

The weight-average molecular weight (Mw) and number-average molecular weight (Mn) are determined by gel permeation liquid chromatography (THF solvent, calibration curve established with linear polystyrene standards, refractometric detector).

The weight-average molecular weight (Mw) of the polymer used in the composition according to the disclosure is, for example, less than or equal to 300 000; it ranges, for example, from 35 000 to 200 000 and such as from 45 000 to 150 000.

The number-average molecular weight (Mn) of the polymer used in the composition according to the disclosure is, for example, less than or equal to 70 000; it ranges, for example, from 10 000 to 60 000 and such as from 12 000 to 50 000.

The polydispersity index I of the polymer used in the composition according to the disclosure may be greater than 2, for example, greater than 2 and less than or equal to 9, such as greater than or equal to 2.5, for example, ranging from 2.5 to 8, and further such as greater than or equal to 2.8, for example, ranging from 2.8 to 6.

Each block of the polymer used in the composition according to the disclosure is derived from one type of monomer or from several different types of monomers.

This means that each block may comprise a homopolymer or a copolymer; this copolymer constituting the block may in turn be random or alternating.

For example, the intermediate block comprising at least one constituent monomer of the first block and at least one constituent monomer of the second block of the polymer is a random polymer.

In one embodiment, the intermediate block is derived essentially from constituent monomers of the first block and of the second block.

The term "essentially" means at least 85%, such as at least 90%, further such as 95% and even further such as 100%.

In another embodiment, the intermediate block has a glass transition temperature Tg that is between the glass transition temperatures of the first and second blocks.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley, according to the following relationship, known as Fox's law:

$$1/Tg = \sum_i (\varpi_i / Tg_i),$$

wherein $\varpi_i$ is the mass fraction of the monomer i in the block under consideration and $Tg_i$ is the glass transition temperature of the homopolymer of the monomer i.

Unless otherwise indicated, the Tg values indicated for the first and second blocks in the present disclosure are theoretical Tg values.

In one embodiment, the first and second blocks of the polymer are such that the difference between the glass transition temperatures of the first and second blocks is generally greater than 10° C., such as greater than 20° C. and further such as greater than 30° C.

The first block may be chosen, for example, from:
a) a block with a Tg of greater than or equal to 40° C.,
b) a block with a Tg of less than or equal to 20° C.,
c) a block with a Tg of between 20 and 40° C.,
and the second block can be chosen, for example, from the categories a), b) and c) different from the first block.

In the present disclosure, the expression:
"between . . . and . . . " is intended to mean a range of values for which the limits mentioned are excluded, and
"from . . . to . . . " and "ranging from . . . to . . . " are intended to mean a range of values for which the limits are included.
a) Block with a Tg of Greater than or Equal to 40° C.

The block with a Tg of greater than or equal to 40° C. has, for example, a Tg ranging from 40 to 150° C., such as greater than or equal to 50° C., for example, ranging from 50° C. to 120° C. and further such as greater than or equal to 60° C., for example, ranging from 60° C. to 120° C.

The block with a Tg of greater than or equal to 40° C. may be a homopolymer or a copolymer.

In the case where this block is a homopolymer, it is derived from a monomer whose homopolymer has a glass transition temperature of greater than or equal to 40° C.

In the case where the first block is a copolymer, it may be totally or partially derived from one or more monomers, the nature and concentration of which are chosen such that the Tg of the resulting copolymer is greater than or equal to 40° C. The copolymer may comprise, for example:

monomers whose homopolymer has a Tg value of greater than or equal to 40° C., for example a Tg ranging from 40 to 150° C., such as greater than or equal to 50° C., for example ranging from 50° C. to 120° C. and further such as greater than or equal to 60° C., for example ranging from 60° C. to 120° C., and monomers whose homopolymer has a Tg value of less than 40° C., chosen from monomers whose homopolymer has a Tg of between 20 and 40° C. and monomers whose homopolymer has a Tg of less than or equal to 20° C., for example a Tg ranging from −100 to 20° C., such as less than 15° C., for example, ranging from −80° C. to 15° C. and further such as less than 10° C., for example, ranging from −50° C. to 0° C., as described later.

The monomers whose homopolymer has a glass transition temperature of greater than or equal to 40° C. are chosen, for example, from the following monomers, also known as the main monomers:

methacrylates of formula $CH_2=C(CH_3)-COOR_1$
wherein $R_1$ is chosen from linear and branched unsubstituted alkyl groups comprising from 1 to 4 carbon atoms, such as a methyl, ethyl, propyl and isobutyl groups or $R_1$ is chosen from $C_4$ to $C_{12}$ cycloalkyl groups, acrylates of formula $CH_2=CH-COOR_2$
wherein $R_2$ is chosen from $C_4$ to $C_{12}$ cycloalkyl groups such as an isobornyl group, and a tert-butyl group, (meth)acrylamides of formula:

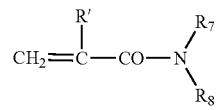

wherein $R_7$ and $R_8$, which may be identical or different, are each chosen from a hydrogen atom and linear and branched $C_1$ to $C_{12}$ alkyl groups such as an n-butyl, t-butyl, isopropyl, isohexyl, isooctyl and isononyl groups; or $R_7$ is H and $R_8$ is a 1,1-dimethyl-3-oxobutyl group, and R' is chosen from H and a methyl group. Examples of monomers that may be mentioned include N-butylacrylamide, N-t-butylacrylamide, N-isopropylacrylamide, N,N-dimethylacrylamide and N,N-dibutylacrylamide, and mixtures thereof.

The main monomers are chosen, for example, from methyl methacrylate, isobutyl(meth)acrylate and isobornyl(meth)acrylate, and mixtures thereof.
b) Block with a Tg of Less than or Equal to 20° C.

The block with a Tg of less than or equal to 20° C. has, for example, a Tg ranging from −100 to 20° C., such as less than or equal to 15° C., for example, ranging from −80° C. to 15° C. and further such as less than or equal to 10° C., for example, ranging from −50° C. to 0° C.

The block with a Tg of less than or equal to 20° C. may be a homopolymer or a copolymer.

In the case where this block is a homopolymer, it is derived from monomers which are such that the homopolymers prepared from these monomers have glass transition temperatures of less than or equal to 20° C. This second block may be, for example, a homopolymer consisting of only one type of monomer (for which the Tg of the corresponding homopolymer is less than or equal to 20° C.).

In the case where the block with a Tg of less than or equal to 20° C. is a copolymer, it may be totally or partially derived from one or more monomers, the nature and concentration of which are chosen such that the Tg of the resulting copolymer is less than or equal to 20° C.

It may comprise, for example at least one monomer whose corresponding homopolymer has a Tg of less than or equal to 20° C., for example, ranging from −100° C. to 20° C., such as less than 15° C., for example, ranging from −80° C. to 15° C. and further such as less than 10° C., for example, ranging from −50° C. to 0° C., and at least one monomer whose corresponding homopolymer has a Tg of greater than 20° C., such as monomers with a Tg of greater than or equal to 40° C., for example, a Tg ranging from 40 to 150° C., such as greater than or equal to 50° C., for example, ranging from 50° C. to 120° C. and further such as greater than or equal to 60° C., for example, ranging from 60° C. to 120° C. and/or monomers with a Tg of between 20 and 40° C., as described above.

In one embodiment, the block with a Tg of less than or equal to 20° C. is a homopolymer.

The monomers whose homopolymer has a Tg of less than or equal to 20° C. are chosen, for example, from the following monomers (main monomers):

acrylates of formula $CH_2=CHCOOR_3$,
wherein $R_3$ is chosen from linear and branched $C_1$ to $C_{12}$ unsubstituted alkyl groups, with the exception of the tert-butyl group, in which at least one hetero atom chosen from O, N and S is optionally intercalated,
methacrylates of formula $CH_2=C(CH_3)-COOR_4$,
wherein $R_4$ is chosen from linear and branched $C_6$ to $C_{12}$ unsubstituted alkyl groups, in which at least one hetero atom chosen from O, N and S is optionally intercalated;
vinyl esters of formula $R_5-CO-O-CH=CH_2$
wherein $R_5$ is chosen from linear and branched $C_4$ to $C_{12}$ alkyl groups,
$C_4$ to $C_{12}$ alkyl vinyl ethers, such as methyl vinyl ether and ethyl vinyl ether,
N—($C_4$ to $C_{12}$)alkyl acrylamides, such as N-octylacrylamide,
and mixtures thereof.

The main monomers that can be used for the block with a Tg of less than or equal to 20° C. are chosen, for example, from alkyl acrylates whose alkyl chain comprises from 1 to 10 carbon atoms, with the exception of the tert-butyl group, such as methyl acrylate, isobutyl acrylate and 2-ethylhexyl acrylate, and mixtures thereof.

c) Block with a Tg of Between 20 and 40° C.

The block with a Tg of between 20 and 40° C. may be a homopolymer or a copolymer.

In the case where this block is a homopolymer, it is derived from a monomer (main monomer) whose homopolymer has a glass transition temperature of between 20 and 40° C.

The monomers whose homopolymer has a glass transition temperature of between 20 and 40° C. are chosen, for example, from n-butyl methacrylate, cyclodecyl acrylate, neopentyl acrylate and isodecylacrylamide, and mixtures thereof.

In the case where the block with a Tg of between 20 and 40° C. is a copolymer, it is totally or partially derived from one or more monomers (main monomer) whose nature and concentration are chosen such that the Tg of the resulting copolymer is between 20 and 40° C.

For example, the block with a Tg of between 20 and 40° C. is a copolymer totally or partially derived from:
main monomers whose corresponding homopolymer has a Tg of greater than or equal to 40° C., for example a Tg ranging from 40° C. to 150° C., such as greater than or equal to 50° C., for example ranging from 50 to 120° C. and further such as greater than or equal to 60° C., for example ranging from 60° C. to 120° C., as described above, and
main monomers whose corresponding homopolymer has a Tg of less than or equal to 20° C., for example a Tg ranging from −100 to 20° C., such as less than or equal to 15° C., for example, ranging from −80° C. to 15° C. and further such as less than or equal to 10° C., for example ranging from −50° C. to 0° C., as described above,
wherein the monomers are chosen such that the Tg of the copolymer forming the first block is between 20 and 40° C.

Such main monomers are chosen, for example, from methyl methacrylate, isobornyl acrylate and methacrylate, butyl acrylate and 2-ethylhexyl acrylate, and mixtures thereof.

For example, the proportion of the second block with a Tg of less than or equal to 20° C. ranges from 10% to 85% by weight, such as from 20% to 70% and further such as from 20% to 50% by weight of the polymer.

According to one embodiment, the block polymer used in the composition according to the disclosure is free of styrene. The term "polymer free of styrene" means a polymer comprising less than 10%, such as less than 5%, further such as less than 2% and even further such as less than 1% by weight of, or even contains no, styrene monomeric unit such as monomeric units of styrene and styrene derivatives, for instance methylstyrene, chlorostyrene and chloromethylstyrene.

According to one embodiment, the block polymer of the composition according to the disclosure is derived from aliphatic ethylenic monomers. The term "aliphatic monomer" means a monomer comprising no aromatic groups.

However, each of the blocks may comprise in a small proportion at least one constituent monomer of the other block.

Thus, the first block may comprise at least one constituent monomer of the second block, and vice versa.

Each of the first and/or second blocks may comprise, in addition to the monomers indicated above, at least one other monomer known as additional monomers, which are different from the main monomers mentioned above.

The nature and amount of this or these additional monomer(s) are chosen such that the block in which they are present has the desired glass transition temperature.

The additional monomers are chosen, for example, from:
a) hydrophilic monomers such as:
ethylenically unsaturated monomers comprising at least one functional group chosen from carboxylic and sulfonic acid functional groups, for instance:
acrylic acid, methacrylic acid, crotonic acid, maleic anhydride, itaconic acid, fumaric acid, maleic acid, acrylamidopropanesulfonic acid, vinylbenzoic acid, vinylphosphoric acid, and salts thereof,
ethylenically unsaturated monomers comprising at least one tertiary amine functional group, for instance 2-vinylpyridine, 4-vinylpyridine, dimethylaminoethyl methacrylate, diethylaminoethyl methacrylate and dimethylaminopropylmethacrylamide, and salts thereof,
methacrylates of formula $CH_2=C(CH_3)-COOR_6$
wherein $R_6$ is an alkyl group chosen from linear and branched alkyl groups comprising from 1 to 4 carbon atoms, such as methyl, ethyl, propyl and isobutyl groups, wherein the alkyl group is substituted with at least one substituent chosen from hydroxyl groups (for instance 2-hydroxypropyl methacrylate and 2-hydroxyethyl methacrylate) and halogen atoms (Cl, Br, I and F), such as trifluoroethyl methacrylate,
methacrylates of formula $CH_2=C(CH_3)-COOR_9$,
wherein $R_9$ is an alkyl group chosen from linear and branched $C_6$ to $C_{12}$ alkyl groups in which at least one hetero atom chosen from O, N and S is optionally intercalated, wherein the alkyl group is substituted with at least one substituent chosen from hydroxyl groups and halogen atoms (Cl, Br, I and F);
acrylates of formula $CH_2=CHCOOR_{10}$,
wherein $R_{10}$ is chosen from linear and branched $C_1$ to $C_{12}$ alkyl groups substituted with at least one substituent chosen from hydroxyl groups and halogen atoms (Cl, Br, I and F), such as 2-hydroxypropyl acrylate and 2-hydroxyethyl acrylate, or $R_{10}$ is chosen from $C_1$ to $C_{12}$ alkyl-O-POEs (polyoxyethylene) with repetition of the oxyethylene unit from 5 to 30 times, for example methoxy-POE, or
$R_{10}$ is chosen from polyoxyethylenated groups comprising from 5 to 30 ethylene oxide units,
b) ethylenically unsaturated monomers comprising at least one silicon atom, such as methacryloxypropyltrimethoxysilane and methacryloxypropyltris(trimethylsiloxy)silane, and mixtures thereof.

In one embodiment, the additional monomers are chosen from acrylic acid, methacrylic acid and trifluoroethyl methacrylate, and mixtures thereof.

The at least one additional monomer may be present in an amount of less than or equal to 30% by weight, for example, from 1% to 30% by weight, such as from 5% to 20% by weight and further such as from 7% to 15% by weight, relative to the total weight of the first and/or second blocks.

According to one embodiment, the polymer used in the composition according to the disclosure is a non-silicone polymer, i.e., a polymer free of silicon atoms.

For example, each of the first and second blocks comprises at least one monomer chosen from (meth)acrylic acid esters as defined above and optionally at least one monomer chosen from (meth)acrylic acids, and mixtures thereof.

In one embodiment, each of the first and second blocks is totally derived from at least one monomer chosen from (meth)acrylic acid esters as defined above and optionally at least one monomer chosen from (meth)acrylic acids, and mixtures thereof.

The polymer used in the composition according to the disclosure may be obtained by free-radical solution polymerization according to the following preparation process:
 a portion of the polymerization solvent is introduced into a suitable reactor and heated until the adequate temperature for the polymerization is reached (typically between 60 and 120° C.),
 once this temperature is reached, the constituent monomers of the first block are introduced in the presence of some of the polymerization initiator,
 after a time T corresponding to a maximum degree of conversion of 90%, the constituent monomers of the second block and the rest of the initiator are introduced,
 the mixture is left to react for a time T' (ranging from 3 to 6 hours), after which the mixture is cooled to room temperature,
 the polymer dissolved in the polymerization solvent is obtained.

The term "polymerization solvent" means a solvent or a mixture of solvents. The polymerization solvent may be chosen, for example, from ethyl acetate, butyl acetate, alcohols such as isopropanol and ethanol, and aliphatic alkanes such as isododecane, and mixtures thereof. In one embodiment, the polymerization solvent is a mixture of butyl acetate and isopropanol or isododecane.

According to a first embodiment, the polymer used in the composition according to the disclosure comprises at least one (such as one) first block with a Tg of greater than or equal to 40° C., as described above in a) and at least one (such as one) second block with a Tg of less than or equal to 20° C., as described above in b).

The first block with a Tg of greater than or equal to 40° C. is, for example, a copolymer derived from monomers whose homopolymer has a glass transition temperature of greater than or equal to 40° C., such as the monomers described above.

The second block with a Tg of less than or equal to 20° C. is, for example, a homopolymer such as a homopolymer derived from monomers as described above.

The proportion of the block with a Tg of greater than or equal to 40° C. ranges, for example, from 20% to 90%, such as from 30% to 80% and further such as from 50% to 70% by weight of the polymer.

The proportion of the block with a Tg of less than or equal to 20° C. ranges, for example, from 5% to 75%, such as from 15% to 50% and further such as from 25% to 45% by weight of the polymer.

Thus, according to a first variant of this embodiment, the polymer used in the composition according to the disclosure may comprise:
 a first block with a Tg of greater than or equal to 40° C., for example, ranging from 70 to 110° C., which is a methyl methacrylate/acrylic acid copolymer,
 a second block with a Tg of less than or equal to 20° C., for example, ranging from 0 to 20° C., which is a methyl acrylate homopolymer, and
 an intermediate block that is a methyl methacrylate/acrylic acid/methyl acrylate copolymer.

According to a second variant, the polymer used in the composition according to the disclosure may comprise:
 a first block with a Tg of greater than or equal to 40° C., for example, ranging from 70 to 100° C., which is a methyl methacrylate/acrylic acid/trifluoroethyl methacrylate copolymer,
 a second block with a Tg of less than or equal to 20° C., for example, ranging from 0 to 20° C., which is a methyl acrylate homopolymer, and
 an intermediate block that is a methyl methacrylate/acrylic acid/methyl acrylate/trifluoroethyl methacrylate random copolymer.

According to a third variant, the polymer used in the composition according to the disclosure may comprise:
 a first block with a Tg of greater than or equal to 40° C., for example, ranging from 85 to 115° C., which is an isobornyl acrylate/isobutyl methacrylate copolymer,
 a second block with a Tg of less than or equal to 20° C., for example, ranging from −85 to −55° C., which is a 2-ethylhexyl acrylate homopolymer, and
 an intermediate block, which is an isobornyl acrylate/isobutyl methacrylate/2-ethylhexyl acrylate random copolymer.

According to a fourth variant, the polymer used in the composition according to the disclosure may comprise:
 a first block with a Tg of greater than or equal to 40° C., for example, ranging from 85 to 115° C., which is an isobornyl acrylate/methyl methacrylate copolymer,
 a second block with a Tg of less than or equal to 20° C., for example, ranging from −85 to −55° C., which is a 2-ethylhexyl acrylate homopolymer, and an intermediate block that is an isobornyl acrylate/methyl methacrylate/2-ethylhexyl acrylate random copolymer.

According to a fifth variant, the polymer used in the composition according to the disclosure may comprise:
a first block with a Tg of greater than or equal to 40° C., for example, ranging from 95 to 125° C., which is an isobornyl acrylate/isobornyl methacrylate copolymer,
a second block with a Tg of less than or equal to 20° C., for example, ranging from −85 to −55° C., which is a 2-ethylhexyl acrylate homopolymer, and
an intermediate block that is an isobornyl acrylate/isobornyl methacrylate/2-ethylhexyl acrylate random copolymer.

According to a sixth variant, the polymer used in the composition according to the disclosure may comprise:
a first block with a Tg of greater than or equal to 40° C., for example, ranging from 85 to 115° C., which is an isobornyl methacrylate/isobutyl methacrylate copolymer,
a second block with a Tg of less than or equal to 20° C., for example, ranging from −35 to −5° C., which is an isobutyl acrylate homopolymer, and
an intermediate block that is an isobornyl methacrylate/isobutyl methacrylate/isobutyl acrylate random copolymer.

According to a seventh variant, the polymer used in the composition according to the disclosure may comprise:
a first block with a Tg of greater than or equal to 40° C., for example ranging from 95 to 125° C., which is an isobornyl acrylate/isobornyl methacrylate copolymer,
a second block with a Tg of less than or equal to 20° C., for example ranging from −35 to −5° C., which is an isobutyl acrylate homopolymer, and
an intermediate block that is an isobornyl acrylate/isobornyl methacrylate/isobutyl acrylate random copolymer.

According to an eighth variant, the polymer used in the composition according to the disclosure may comprise:
a first block with a Tg of greater than or equal to 40° C., for example, ranging from 60 to 90° C., which is an isobornyl acrylate/isobutyl methacrylate copolymer,
a second block with a Tg of less than or equal to 20° C., for example, ranging from −35 to −5° C., which is an isobutyl acrylate homopolymer, and
an intermediate block that is an isobornyl acrylate/isobutyl methacrylate/isobutyl acrylate random copolymer.

According to a second embodiment, the polymer used in the composition according to the disclosure comprises at least one (such as one) first block with a glass transition temperature (Tg) of between 20 and 40° C., in accordance with the blocks described in c) and at least one (such as one) second block with a glass transition temperature of less than or equal to 20° C., as described above in b) or a glass transition temperature of greater than or equal to 40° C., as described in a) above.

The proportion of the first block with a Tg of between 20 and 40° C. ranges, for example, from 10% to 85%, such as from 30% to 80% and further such as from 50% to 70% by weight of the polymer.

When the second block is a block with a Tg of greater than or equal to 40° C., it is, for example, present in a proportion ranging from 10% to 85% by weight, such as from 20% to 70% and further such as from 30% to 70% by weight of the polymer.

When the second block is a block with a Tg of less than or equal to 20° C., it is, for example, present in a proportion ranging from 10% to 85% by weight, such as from 20% to 70% and further such as from 20% to 50% by weight of the polymer.

For example, the first block with a Tg of between 20 and 40° C. is a copolymer derived from monomers which are such that the corresponding homopolymer has a Tg of greater than or equal to 40° C., and from monomers which are such that the corresponding homopolymer has a Tg of less than or equal to 20° C.

The second block with a Tg of less than or equal to 20° C. or with a Tg of greater than or equal to 40° C. is, for example, a homopolymer.

Thus, according to a first variant of this second embodiment, the polymer used in the composition according to the disclosure may comprise:
a first block with a Tg of between 20 and 40° C., for example with a Tg ranging from 25 to 39° C., which is a copolymer comprising at least one methyl acrylate monomer, at least one methyl methacrylate monomer and at least one acrylic acid monomer,
a second block with a Tg of greater than or equal to 40° C., for example, ranging from 85 to 125° C., which is a homopolymer composed of methyl methacrylate monomers, and
an intermediate block comprising at least one monomer chosen from methyl acrylate and methyl methacrylate monomers, and
an intermediate block comprising methyl methacrylate, at least one acrylic acid monomer and at least one methyl acrylate monomer.

According to a second variant of this second embodiment, the polymer used in the composition according to the disclosure may comprise:
a first block with a Tg of between 20 and 40° C., for example, with a Tg ranging from 21 to 39° C., which is a copolymer comprising isobornyl acrylate/isobutyl methacrylate/2-ethylhexyl acrylate,
a second block with a Tg of less than or equal to 20° C., for example, ranging from −65 to −35° C., which is a methyl methacrylate homopolymer, and
an intermediate block that is an isobornyl acrylate/isobutyl methacrylate/2-ethylhexyl acrylate random copolymer.

According to a third variant of this second embodiment, the polymer used in the composition according to the disclosure may comprise:
a first block with a Tg of between 20 and 40° C., for example, with a Tg ranging from 21 to 39° C., which is an isobornyl acrylate/methyl acrylate/acrylic acid copolymer,
a second block with a Tg of greater than or equal to 40° C., for example, ranging from 85 to 115° C., which is an isobornyl acrylate homopolymer, and
an intermediate block that is an isobornyl acrylate/methyl acrylate/acrylic acid random copolymer.

The block polymer described above may be present in the composition according to the disclosure in an amount ranging from 0.1% to 90% by weight, such as from 0.5% to 50% by weight and further such as from 0.5% to 30% by weight, relative to the total weight of the composition.

The composition according to the disclosure comprises at least one silicone oil.

The term "oil" means any non-aqueous medium that is liquid at room temperature (25° C.) and atmospheric pressure (760 mmHg), which is compatible with application to the skin, mucous membranes (the lips) and/or the integuments (nails, eyelashes, eyebrows or hair).

The term "non-volatile oil" means an oil that is capable of remaining on the skin at room temperature (25° C.) and atmospheric pressure for at least one hour and that, for example, has a non-zero vapor pressure at room temperature (25° C.) and atmospheric pressure, of less than 0.01 mmHg (1.33 Pa).

The non-volatile silicone oil has, for example, a viscosity ranging from 10 to 10 000 cSt such as from 10 to 5000 cSt.

The non-volatile silicone oil may be chosen from non-volatile polydimethylsiloxanes (PDMSs); polydimethylsiloxanes comprising at least one group chosen from alkyl, alkoxy and phenyl groups, pendent or at the end of a silicone chain, wherein the at least one group comprises from 2 to 24 carbon atoms; phenyl silicones, for instance phenyl trimethicones, phenyl dimethicones, phenyltrimethylsiloxydiphenylsiloxanes, diphenyl dimethicones and diphenylmethyldiphenyltrisiloxanes; polysiloxanes modified with at least one entity chosen from fatty acids (such as those of $C_8$-$C_{20}$), fatty alcohols (such as those of $C_8$-$C_{20}$) and polyoxyalkylenes (such as polyoxyethylene and polyoxypropylene); amino silicones; silicones comprising at least one hydroxyl group; fluoro silicones comprising at least one fluoro group that is pendent or at the end of a silicone chain, comprising from 1 to 12 carbon atoms, at least one of the hydrogens of which is replaced with a fluorine atom and mixtures thereof.

For example, the non-volatile silicone oil is chosen from non-volatile phenyl silicone oils.

The non-volatile phenyl silicone oil may be chosen from the phenyl silicones of formula (VI) below:

$$\text{(VI)}\quad R_9-\underset{R_2}{\underset{|}{\overset{R_1}{\overset{|}{Si}}}}-O-\left[\underset{R_4}{\underset{|}{\overset{R_3}{\overset{|}{Si}}}}-O\right]_p-\left[\underset{R_8}{\underset{|}{\overset{Ph}{\overset{|}{Si}}}}-O\right]_q-\left[\underset{Ph}{\underset{|}{\overset{Ph}{\overset{|}{Si}}}}-O\right]_n-\underset{\underset{Si-(R_{10})_3}{\underset{|}{O}}}{\overset{R_5}{\overset{|}{Si}}}-O-\underset{R_7}{\underset{|}{\overset{R_5}{\overset{|}{Si}}}}-R_6$$

wherein $R_1$ to $R_{10}$, which may be identical or different, are each chosen from saturated and unsaturated, linear, cyclic and branched $C_1$-$C_{30}$ hydrocarbon-based radicals, m, n, p and q, which may be identical or difference, are each chosen from integers ranging from 0 to 900, with the proviso that the sum "m+n+q" is other than 0.

For example, the sum "m+n+q" ranges from 1 to 100.

Further for example, the sum "m+n+p+q" ranges from 1 to 900 such as from 1 to 800.

Even further for example, q is equal to 0.

In one embodiment, the non-volatile phenyl silicone oil is chosen from the phenyl silicones of formula (VII) below:

$$\text{(VII)}\quad H_3C-\underset{R_2}{\underset{|}{\overset{R_1}{\overset{|}{Si}}}}-O-\left[\underset{R_4}{\underset{|}{\overset{R_3}{\overset{|}{Si}}}}-O\right]_p-\left[\underset{Ph}{\underset{|}{\overset{Ph}{\overset{|}{Si}}}}-O\right]_n-\left[\underset{\underset{Si(CH_3)_3}{\underset{|}{O}}}{\overset{Ph}{\overset{|}{Si}}}-O\right]_m-\underset{R_6}{\underset{|}{\overset{R_5}{\overset{|}{Si}}}}-CH_3$$

wherein:

R1 to R6, which may be identical or different, are each chosen from saturated and unsaturated, linear, cyclic and branched $C_1$-$C_{30}$ hydrocarbon-based radicals, and m, n and p, which may be identical or different, are each chosen from integers ranging from 0 to 100, with the proviso that the sum "n+m" ranges from 1 to 100.

For example, R1 to R6, which may be identical or different, are each chosen from saturated linear and branched $C_1$-$C_{30}$ such as $C_1$-$C_{12}$ hydrocarbon-based radicals, for example, methyl, ethyl, propyl and butyl radicals.

R1 to R6 may, for example, be identical, and may also be a methyl radical.

It is possible to have, for example, m=1, 2 or 3, and/or n=0 and/or p=0 or 1.

The phenyl silicone oils may be chosen, for example, from phenyl trimethicones, phenyl dimethicones, phenyl trimethylsiloxy diphenylsiloxanes, diphenyl dimethicones and diphenyl methyldiphenyl trisiloxanes, and mixtures thereof.

The weight-average molecular weight of the phenyl silicone oil ranges, for example, from 500 to 10 000.

In one embodiment, the phenyl silicone oil used is a phenyl silicone oil of formula (VI) with a viscosity at 25° C. ranging from 5 to 1500 mm²/s (i.e., 5 to 1500 cSt), such as from 5 to 1000 mm²/s (i.e., 5 to 1000 cSt).

Non-volatile phenyl silicone oils that may be used include, for example, phenyl trimethicones such as DC556 from Dow Corning (22.5 cSt), the oil Silbione 70663V30 from Rhône-Poulenc (28 cSt), and diphenyl dimethicones such as the Belsil oils, for example, Belsil PDM1000 (1000 cSt), Belsil PDM 200 (200 cSt) and Belsil PDM 20 (20 cSt) from Wacker. The values in parentheses represent the viscosities at 25° C.

The non-volatile silicone oil may be present in the composition according to the disclosure in an amount ranging, for example, from 30% to 95% by weight, such as from 40% to 85% by weight and further such as from 50% to 80% by weight, relative to the total weight of the non-volatile liquid fatty phase.

The non-volatile silicone oil may be present in the composition according to the disclosure in an amount ranging, for example, from 0.1% to 70% by weight, such as from 1% to 50% by weight and further such as from 1% to 30% by weight, relative to the total weight of the composition.

According to one embodiment, the organic liquid medium of the composition comprises at least one organic liquid that is the or one of the organic solvent(s) for polymerization of the block polymer as described above. For example, the organic polymerization solvent is the organic liquid that is in majority amount by weight in the organic liquid medium of the cosmetic composition.

The non-volatile liquid fatty phase of the composition according to the disclosure may also comprise at least one non-silicone non-volatile oil, such as a non-volatile hydrocarbon-based oil. For example, the oily non-volatile liquid fatty phase is macroscopically homogeneous, i.e., homogeneous to the naked eye.

The term "hydrocarbon-based oil" means an oil formed essentially from, or consisting of, carbon and hydrogen atoms, and possibly oxygen or nitrogen atoms, and containing no silicon or fluorine atoms. It may comprise at least one group chosen from alcohol, ester, ether, carboxylic acid, amine and amide groups.

The non-silicone non-volatile oil may be present in an amount ranging, for example, from 0.1% to 70% by weight, such as from 0.5% to 60% by weight and further such as from 1% to 50% by weight, relative to the total weight of the non-volatile liquid fatty phase.

The non-silicone non-volatile oil may be present in the composition according to the disclosure in an amount ranging from 0.1% to 60% by weight, such as from 0.5% to 30% by weight and further such as from 1% to 20% by weight, relative to the total weight of the composition.

Non-silicone non-volatile oils that may be used include, for example, non-volatile hydrocarbon-based oils such as liquid paraffin (or petroleum jelly), squalane, hydrogenated polyisobutylene (parleam oil), perhydrosqualene, mink oil, turtle oil, soybean oil, sweet almond oil, beauty-leaf oil, palm oil, grapeseed oil, sesame seed oil, maize oil, arara oil, rapeseed oil, sunflower oil, cotton seed oil, apricot oil, castor oil, avocado oil, jojoba oil, olive oil and cereal germ oil; lanolic acid, oleic acid, lauric acid and stearic acid esters; fatty esters, for example, those of $C_{12}$-$C_{36}$, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate and lactate, bis(2-ethylhexyl) succinate, diisostearyl malate, and glyceryl and diglyceryl triisostearates; higher fatty acids, for example, those of $C_{14}$-$C_{22}$, such as myristic acid, palmitic acid, stearic acid, behenic acid, oleic acid, linoleic acid, linolenic acid and isostearic acid; higher fatty alcohols, for example, those of $C_{16}$-$C_{22}$, such as cetanol, oleyl alcohol, linoleyl alcohol, linolenyl alcohol, isostearyl alcohol and octyldodecanol; and mixtures thereof.

For example, the non-silicone non-volatile oil is chosen from hydrocarbons, such as alkanes, for instance hydrogenated polyisobutene.

The composition according to the disclosure may also comprise at least one volatile oil.

The term "volatile oil" means any non-aqueous medium that is capable of evaporating from the skin or the lips in less than one hour, and which has, for example, a vapour pressure, at room temperature and atmospheric pressure, ranging from 10-3 to 300 mmHg (0.13 Pa to 40 000 Pa).

According to the disclosure, one or more volatile oils may be used.

These oils may be hydrocarbon-based oils or silicone oils optionally comprising at least one group chosen from alkyl and alkoxy groups that is pendent or at the end of a silicone chain.

As volatile silicone oils that may be used herein, mention may be made, for example, of linear or cyclic silicones comprising from 2 to 7 silicon atoms, these silicones optionally comprising at least one group chosen from alkyl and alkoxy groups comprising from 1 to 10 carbon atoms. As volatile silicone oils that may be used herein, mention may be made, for example, of octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane and decamethyltetrasiloxane, and mixtures thereof.

As other volatile oils that may be used herein, examples include $C_8$-$C_{16}$ isoalkane oils (also known as isoparaffins), for instance isododecane, isodecane and isohexadecane and, for example, the oils sold under the trade names Isopar and Permethyl, such as isododecane (Permethyl 99A).

The volatile oil may be present in the composition according to the disclosure in an amount ranging from 0.1% to 90% by weight, such as from 1% to 70% by weight and further such as from 5% to 50% by weight, relative to the total weight of the composition.

The composition may comprise, besides the block polymer described above according to the disclosure, at least one additional polymer such as a film-forming polymer. According to the present disclosure, the term "film-forming polymer" means a polymer that is capable, by itself or in the presence of an auxiliary film-forming agent, of forming a continuous film that adheres to a support, such as to keratin materials.

Among the film-forming polymers that may be used in the composition as disclosed herein, mention may be made, for example, of synthetic polymers, free-radical type or polycondensate type, and polymers of natural origin, and mixtures thereof. Film-forming polymers that may be mentioned include, for example, acrylic polymers, polyurethanes, polyesters, polyamides, polyureas and cellulose-based polymers, for instance nitrocellulose.

The composition according to the disclosure may also comprise at least some fatty substances that are solid at room temperature, chosen, for example, from waxes, pasty fatty substances and gums, and mixtures thereof. These fatty substances may be of animal, plant, mineral or synthetic origin.

For the purposes of the present disclosure, the term "wax" means a lipophilic compound that is solid at room temperature (25° C.), which undergoes a reversible solid/liquid change of state, and which has a melting point of greater than or equal to 30° C., which may be up to 120° C.

By bringing the wax to the liquid state (melting), it is possible to make it miscible with the oils possibly present and to form a microscopically homogeneous mixture, but, on returning the temperature of the mixture to room temperature, recrystallization of the wax is obtained in the oils of the mixture. The melting point of the wax may be measured using a differential scanning calorimeter (DSC), for example, the calorimeter sold under the name DSC 30 by the company Mettler.

The wax may also have a hardness ranging from 0.05 MPa to 15 MPa, such as from 6 MPa to 15 MPa. The hardness is determined by measuring the compressive force, measured at 20° C. using the texturometer sold under the name TA-XT2i by the company Rheo, equipped with a stainless-steel cylinder 2 mm in diameter travelling at a measuring speed of 0.1 mm/s and penetrating the wax to a penetration depth of 0.3 mm.

The waxes may be chosen, for example, from hydrocarbon-based waxes, fluoro waxes and silicone waxes and may be of plant, mineral, animal and/or synthetic origin. For example, the waxes have a melting point of greater than 25° C. such as greater than 45° C.

As waxes that may be used in the composition as disclosed herein, mention may be made, for example, of beeswax, carnauba wax and candelilla wax, paraffin, microcrystalline waxes, ceresin and ozokerite, synthetic waxes, for instance polyethylene waxes and Fischer-Tropsch waxes, and silicone waxes, for instance alkyl and alkoxy dimethicones comprising from 16 to 45 carbon atoms.

The gums are generally chosen from polydimethylsiloxanes (PDMSs) of high molecular weight and cellulose gums and polysaccharides, and the pasty substances are generally chosen from hydrocarbon-based compounds, for instance lanolins and derivatives thereof, and PDMSs.

The nature and amount of the solid substances in the composition as disclosed herein depend on the desired mechanical properties and textures. As a guide, the composition may comprise from 0.1% to 50% by weight such as from 1% to 30% by weight of waxes relative to the total weight of the composition.

The composition according to the disclosure may also comprise at least one dyestuff chosen from water-soluble dyes and pulverulent dyestuffs, for instance pigments, nacres and flakes that are well known to those skilled in the art. The at least one dyestuff may be present in the composition in an amount ranging from 0.01% to 50% by weight such as from 0.01% to 30% by weight relative to the weight of the composition.

The term "pigments" means white or colored, mineral or organic particles of any shape, which are insoluble in the physiological medium and which are intended to color the composition.

The term "nacres" means iridescent particles of any shape, produced, for example, by certain molluscs in their shell, or alternatively synthesized.

The pigments may be white or colored, and mineral and/or organic. Among the mineral pigments that may be mentioned, examples include titanium dioxide, optionally surface-treated, zirconium oxide and cerium oxide, and also zinc oxide, iron oxide (black, yellow and red) and chromium oxide, manganese violet, ultramarine blue, chromium hydrate and ferric blue, and metal powders, for instance aluminium powder and copper powder.

Among the organic pigments that may be mentioned, examples include carbon black, pigments of D & C type, and lakes based on cochineal carmine or on barium, strontium, calcium or aluminium.

Mention may also be made of pigments with an effect, such as particles comprising a substrate chosen from natural and synthetic, organic and mineral substrates, for example, glass, acrylic resins, polyester, polyurethane, polyethylene terephthalate, ceramics and aluminas, wherein the substrate is uncoated or coated with metal substances, for instance aluminium, gold, silver, platinum, copper and bronze, or with metal oxides, for instance titanium dioxide, iron oxide and chromium oxide, and mixtures thereof.

The nacreous pigments may be chosen from white nacreous pigments such as mica coated with titanium or with bismuth oxychloride, colored nacreous pigments such as titanium mica coated with iron oxides, titanium mica coated, for example, with ferric blue or chromium oxide, titanium mica coated with an organic pigment of the abovementioned type and also nacreous pigments based on bismuth oxychloride. Interference pigments, such as liquid-crystal pigments and multilayer pigments, may also be used.

The water-soluble dyes are chosen, for example, from beetroot juice and methylene blue.

The composition according to the disclosure may also comprise at least one filler, in an amount ranging, for example, from 0.01% to 50% by weight such as from 0.01% to 30% by weight, relative to the total weight of the composition. The term "fillers" means colorless or white, mineral or synthetic particles of any shape, which are insoluble in the medium of the composition, irrespective of the temperature at which the composition is manufactured. These fillers serve, for example, to modify the rheology and/or the texture of the composition.

The fillers may be mineral or organic in any form, platelet-shaped, spherical or oblong, irrespective of the crystallographic form (for example, leaflet, cubic, hexagonal, orthorhombic, etc.). Mention may be made, for example, of talc, mica, silica, kaolin, polyamide (Nylon®) powders (Orgasol® from Atochem), poly-β-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Exapancel® (Nobel Industrie) and acrylic acid copolymers (Polytrap® from the company Dow Corning) and silicone resin microbeads (for example Tospearls® from Toshiba), elastomeric polyorganosiloxane particles, precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids comprising from 8 to 22 carbon atoms such as from 12 to 18 carbon atoms, for example, zinc, magnesium and lithium stearates, zinc laurate, and magnesium myristate.

The composition may comprise a hydrophilic medium comprising water or a mixture of water and at least one hydrophilic organic solvent, for instance alcohols chosen, for example, from linear and branched lower monoalcohols comprising from 2 to 5 carbon atoms, for instance ethanol, isopropanol and n-propanol, and polyols, for instance glycerol, diglycerol, propylene glycol, sorbitol and pentylene glycol, and polyethylene glycols, and hydrophilic $C_2$ ethers and $C_2$-$C_4$ aldehydes.

The water or the mixture of water and at least one hydrophilic organic solvent may be present in the composition according to the disclosure in an amount ranging from 0.1% to 99% by weight such as from 10% to 80% by weight relative to the total weight of the composition.

The composition according to the disclosure may also comprise at least one ingredient chosen from the ingredients commonly used in cosmetics, such as vitamins, thickeners, trace elements, softeners, sequestering agents, fragrances, acidifying and basifying agents, preserving agents, sunscreens, surfactants, antioxidants, agents for preventing hair loss, antidandruff agents and propellants, and mixtures thereof.

Needless to say, a person skilled in the art will take care to select this or these optional additional compound(s), and/or the amount thereof, such that the advantageous properties of the corresponding composition according to the disclosure are not, or are not substantially, adversely affected by the envisaged addition.

The composition according to the disclosure may, for example, be in the form of a suspension, a dispersion, a solution, a gel, an emulsion, such as an oil-in-water (O/W) emulsion, a water-in-oil (W/O) emulsion and a multiple emulsion (W/O/W, polyol/O/W and O/W/O emulsions), in the form of a cream, a mousse, a stick, a dispersion of vesicles, such as a dispersion of ionic or nonionic lipids, a two-phase or multi-phase lotion, a spray, a powder, a paste, such as a soft paste (for example, a paste with a dynamic viscosity at 25° C. of about from 0.1 to 40 Pa·s under a shear rate of 200 s$^{-1}$, after measurement for 10 minutes in cone/plate geometry). The composition may be anhydrous; for example, it may be an anhydrous stick or paste. The composition may be a leave-in composition.

A person skilled in the art may select the appropriate presentation form, and also the method for preparing it, on the basis of his or her general knowledge, taking into account firstly the nature of the constituents used, such as their solubility in the support, and secondly the intended application for the composition.

Further disclosed herein is a cosmetic assembly comprising:
i) a container delimiting at least one compartment, wherein the container is closed by a closing member; and
ii) a composition placed inside the compartment, wherein the composition is in accordance with the present disclosure.

The container may be in any adequate form. It may, for example, be in the form of a bottle, a tube, a jar, a case, a box, a sachet or a carton.

The closing member may be in the form of a removable stopper, a lid, a cap, a tear-off strip or a capsule, such as that of the type comprising a body attached to the container and a cover cap articulated on the body. It may also be in the form of a member for selectively closing the container, such as a pump, a valve and a flap valve.

The container may be combined with an applicator, such as in the form of a brush comprising an arrangement of bristles maintained by a twisted wire. Such a twisted brush is described, for example, in U.S. Pat. No. 4,887,622. It may also be in the form of a comb comprising a plurality of application members, obtained, for example, by moulding. Such combs are described, for example, in French patent FR 2 796 529. The applicator may be in the form of a fine brush, as described, for example, in French patent FR 2 722 380. The applicator may be in the form of a block of foam or of elastomer, a felt or a spatula. The applicator may be free (tuft or sponge) or securely fastened to a rod borne by the closing member, as described, for example, in U.S. Pat. No. 5,492,426. The applicator may be securely fastened to the container, as described, for example, in French patent FR 2 761 959.

The product may be contained directly in the container, or indirectly. By way of example, the product may be arranged on an impregnated support, such as in the form of a wipe or a pad, and arranged (individually or in plurality) in a box or in a sachet. Such a support incorporating the product is described, for example, in patent application WO 01/03538.

The closing member may be coupled to the container by screwing. Alternatively, the coupling between the closing member and the container is done other than by screwing, such as via a bayonet mechanism, by click-fastening, gripping, welding, bonding or by magnetic attraction. The term "click-fastening" means any system involving the crossing of a bead or cord of material by elastic deformation of a portion, such as of the closing member, followed by return to the elastically unconstrained position of the portion after the crossing of the bead or cord.

The container may be at least partially made of thermoplastic material. Examples of thermoplastic materials that may be mentioned include polypropylene and polyethylene.

Alternatively, the container is made of non-thermoplastic material, such as glass and metal (and alloy).

The container may have rigid walls or deformable walls, such as in the form of a tube and a tubular bottle.

The container may comprise means for distributing or facilitating the distribution of the composition. By way of example, the container may have deformable walls so as to allow the composition to exit in response to a positive pressure inside the container, wherein this positive pressure is caused by elastic (or non-elastic) squeezing of the walls of the container. Alternatively, when the product is in the form of a stick, the product may be driven out by a piston mechanism. Still in the case of a stick, such as a stick of makeup product (for example, lipstick, foundation, etc.), the container may comprise a mechanism, such as a rack mechanism, a threaded-rod mechanism and a helical groove mechanism, and may be capable of moving a stick in the direction of the said aperture. Such a mechanism is described, for example, in French patent FR 2 806 273 and in French patent FR 2 775 566. Such a mechanism for a liquid product is described in French patent FR 2 727 609.

The container may, for example, consist of a carton with a base delimiting at least one housing containing the composition, and a lid, for example, articulated on the base, and capable of at least partially covering the base. Such a carton is described, for example, in patent application WO 03/018423 or in French patent FR 2 791 042.

The container may be equipped with a drainer arranged in the region of the aperture of the container. Such a drainer makes it possible to wipe the applicator and possibly the rod to which it may be securely fastened. Such a drainer is described, for example, in French patent FR 2 792 618.

The composition may be at atmospheric pressure inside the container (at room temperature) or pressurized, such as by means of a propellent gas (aerosol). When the composition is pressurized, the container is equipped with a valve (of the type used for aerosols).

The content of the patents or patent applications mentioned above are incorporated by reference into the present patent application.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The invention is illustrated in greater detail by the non-limiting examples described below.

EXAMPLE 1

Preparation of a poly(isobornyl acrylate/isobornyl methacrylate/2-ethylhexyl acrylate) polymer 100 g of isododecane were introduced into a 1 liter reactor and the temperature was then increased so as to pass from room temperature (25° C.) to 90° C. over 1 hour.

105 g of isobornyl acrylate, 105 g of isobornyl methacrylate, 110 g of isododecane and 1.8 g of 2,5-bis(2-ethylhexanoylperoxy)-2,5-dimethylhexane (Trigonox® 141 from Akzo Nobel) were then added, at 90° C. and over 1 hour.

The mixture was maintained at 90° C. for 1 hour 30 minutes.

90 g of 2-ethylhexyl acrylate, 90 g of isododecane and 1.2 g of 2,5-bis(2-ethylhexanoylperoxy)-2,5-dimethylhexane were then introduced into the above mixture, still at 90° C. and over 30 minutes.

The mixture was maintained at 90° C. for 3 hours and was then cooled.

A solution containing 50% polymer active material in isododecane was obtained.

A polymer comprising a poly(isobornyl acrylate/isobornyl methacrylate) first block with a Tg of 110° C., a poly-2-ethylhexyl acrylate second block with a Tg of −70° C. and an intermediate block that is an isobornyl acrylate/isobornyl methacrylate/2-ethylhexyl acrylate random polymer was obtained.

This polymer has a weight-average molecular weight of 103 900 and a number-average molecular weight of 21 300, i.e. a polydispersity index I of 4.89.

EXAMPLE 2

A lipstick having the composition below was prepared:

| | |
|---|---|
| Block polymer of Example 1 at 50% by weight in isododecane | 65 g |
| Hydrogenated polyisobutylene (parleam oil) | 2.1 g |
| Octyldodecanol | 0.9 g |
| Phenyl silicone oil (Dow Corning 556C) | 27.8 g |
| Polyvinylpyrrolidone/eicosene copolymer (Antaron V220 from ISP) | 1.2 g |
| Pigments | 3 g |

The octyldodecanol, the silicone oil, the parleam oil, the sucrose acetate isobutyrate and the polyvinylpyrrolidone/eicosene copolymer were mixed together with heating at about 60° C. A ground pigmentary mixture of the pigments was made with this mixture by the grinding the mixture three times in a three-roll mill.

The ground pigmentary mixture, the isododecane and the block polymer were then mixed together at room temperature and the silica was then finally introduced. The formulation was then introduced into a leaktight heating bottle.

The transfer-resistance properties of the makeup film obtained with this lipstick were then evaluated, by using the following protocol:

A support (rectangle of 40 mm×70 mm and 3 mm thick) of polyethylene foam that is adhesive on one of the faces, having a density of 33 kg/m$^3$ (sold under the name RE40X70EP3 from the company Joint Technique Lyonnais Ind) was preheated on a hotplate maintained at a temperature of 40° C. in order for the surface of the support to be maintained at a temperature of 33° C.±1° C.

While leaving the support on the hotplate, the composition was applied over the entire non-adhesive surface of the support, by spreading it using a fine brush to obtain a deposit of about 15 μm of the composition, and the support was then left to dry for 30 minutes.

After drying, the support was bonded via its adhesive face onto an anvil of diameter 20 mm and equipped with a screw pitch. The support/deposit assembly was then cut up using a punch 18 mm in diameter. The anvil was then screwed onto a press (Statif Manuel Imada SV-2 from the company Someco) equipped with a tensile testing machine (Imada DPS-20 from the company Someco).

White photocopier paper of 80 g/m$^2$ was placed on the bed of the press and the support/deposit assembly was then pressed on the paper at a pressure of 2.5 kg for 30 seconds. After removing the support/deposit assembly, some of the deposit was transferred onto the paper. The color of the deposit transferred onto the paper was then measured using a Minolta CR300 colorimeter, wherein the color is characterized by the L*, a*, b* colorimetric parameters. The calorimetric parameters L*$_0$, a*$_0$ and b*$_0$ of the color of the plain paper used was determined.

The difference in color ΔE1 between the color of the deposit transferred relative to the color of the plain paper was then determined by means of the following relationship.

$$\Delta E1 = \sqrt{(L^* - L_0^*)^2 + (a^* - a_0^*)^2 + (b^* - b_0^*)^2}$$

Moreover, a total transfer reference was prepared by applying the composition directly onto a paper identical to the one used previously, at room temperature (25° C.), by spreading the composition using a fine brush and so as to obtain a deposit of about 15 μm of the composition, and the deposit was then left to dry for 30 minutes at room temperature (25° C.). After drying, the colorimetric parameters L*', a*' and b*' of the color of the deposit placed on the paper, corresponding to the reference color of total transfer, was measured directly. The colorimetric parameters L*'$_0$, a*'$_0$ and b*'$_0$ of the colour of the plain paper used were determined.

The difference in color ΔE2 between the reference color of total transfer relative to the color of the plain paper was then determined by means of the following relationship.

$$\Delta E2 = \sqrt{(L^{*'} - L_0^{*'})^2 + (a^{*'} - a_0^{*'})^2 + (b^{*'} - b_0^{*'})^2}$$

The transfer of the composition, expressed as a percentage, is equal to the ratio:

ΔE1/ΔE2×100

The measurement was performed on 4 supports in succession and the transfer value corresponds to the mean of the 4 measurements obtained with the 4 supports.

The lipstick of Example 2 forms a film having a transfer of 18%±2%.

EXAMPLE 3

A lipstick, not in accordance with the invention, having the composition below was prepared:

| | |
|---|---|
| Block polymer of Example 1 at 50% by weight in isododecane | 65 g |
| Hydrogenated polyisobutylene (parleam oil) | 27.8 g |
| Octyldodecanol | 0.9 g |
| Phenyl silicone oil (Dow Corning 556C) | 2.1 g |
| Polyvinylpyrrolidone/eicosene copolymer (Antaron V220 from ISP) | 1.2 g |
| Pigments | 3 g |

This lipstick, compared with the lipstick of Example 2, has a much lower amount of non-volatile silicone oil (2.1% instead of 27.8%) and a much higher amount of parleam oil (27.8% instead of 2.1%).

The film obtained with this lipstick has a transfer resistance, measured according to the same protocol described in Example 2, of 54%+1%. This lipstick thus has poorer transfer-resistance properties than the lipstick of Example 2 according to the invention.

What is claimed is:

1. A cosmetic composition comprising at least one block polymer and a cosmetically acceptable organic liquid medium comprising a non-volatile liquid fatty phase, wherein:

the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:
   a) a block with a Tg of greater than or equal to 40° C.,
   b) a block with a Tg of less than or equal to 20° C.,
   c) a block with a Tg of between 20 and 40° C., and
the at least one second block is chosen from a category a), b) or c) different from the at least one first block,
   the non-volatile liquid fatty phase comprises at least 30% by weight of at least one non-volatile silicone oil, relative to the total weight of the non-volatile liquid fatty phase, and
   the at least one block polymer is non-elastomeric.

2. The composition according to claim 1, wherein the at least one block polymer is free of styrene.

3. The composition according to claim 1, wherein the first and second blocks are mutually incompatible.

4. The composition according to claim 1, wherein the at least one block polymer comprises at least one first block with a glass transition temperature (Tg) of greater than or equal to 40° C. and at least one second block with a glass transition temperature of less than or equal to 20° C.

5. The composition according to claim 4, wherein the at least one first block with a Tg of greater than or equal to 40° C. is present in an amount ranging from 20% to 90% by weight relative to the total weight of the at least one block polymer.

6. The composition according to claim 5, wherein the at least one first block with a Tg of greater than or equal to 40° C. is present in an amount ranging from 30% to 80% by weight relative to the total weight of the at least one block polymer.

7. The composition according to claim 6, wherein the at least one first block with a Tg of greater than or equal to 40° C. is present in an amount ranging from 50% to 70% by weight relative to the total weight of the at least one block polymer.

8. The composition according to claim 4, wherein the at least one second block with a Tg of less than or equal to 20° C. is present in an amount ranging from 5% to 75% by weight relative to the total weight of the at least one block polymer.

9. The composition according to claim 8, wherein the at least one second block with a Tg of less than or equal to 20° C. is present in an amount ranging from 15% to 50% by weight relative to the total weight of the at least one block polymer.

10. The composition according to claim 9, wherein the at least one second block with a Tg of less than or equal to 20° C. is present in an amount ranging from 25% to 45% by weight relative to the total weight of the at least one block polymer.

11. The composition according to claim 1, wherein the at least one block polymer comprises at least one first block with a glass transition temperature (Tg) of between 20 and 40° C. and at least one second block with a glass transition temperature of less than or equal to 20° C. or a glass transition temperature of greater than or equal to 40° C.

12. The composition according to claim 11, wherein the at least one first block with a Tg of between 20 and 40° C. is present in an amount ranging from 10% to 85% by weight relative to the total weight of the at least one block polymer.

13. The composition according to claim 12, wherein the at least one first block with a Tg of between 20 and 40° C. is present in an amount ranging from 30% to 80% by weight relative to the total weight of the at least one block polymer.

14. The composition according to claim 13, wherein the at least one first block with a Tg of between 20 and 40° C. is present in an amount ranging from 50% to 70% by weight relative to the total weight of the at least one block polymer.

15. The composition according to claim 11, wherein the at least one second block has a Tg of greater than or equal to 40° C.

16. The composition according to claim 15, wherein the at least one second block with a Tg of greater than or equal to 40° C. is present in an amount ranging from 10% to 85% by weight relative to the total weight of the at least one block polymer.

17. The composition according to claim 16, wherein the at least one second block with a Tg of greater than or equal to 40° C. is present in an amount ranging from 20% to 70% by weight relative to the total weight of the at least one block polymer.

18. The composition according to claim 17, wherein the at least one second block with a Tg of greater than or equal to 40° C. is present in an amount ranging from 30% to 70% by weight relative to the total weight of the at least one block polymer.

19. The composition according to claim 11, wherein the at least one second block has a Tg of less than or equal to 20° C.

20. The composition according to claim 1, wherein the block with a glass transition temperature of less than or equal to 20° C. is present in an amount ranging from 20% to 90% by weight relative to the total weight of the at least one block polymer.

21. The composition according to claim 20, wherein the block with a glass transition temperature of less than or equal to 20° C. is present in an amount ranging from 30% to 80% by weight relative to the total weight of the at least one block polymer.

22. The composition according to claim 21, wherein the block with a glass transition temperature of less than or equal to 20° C. is present in an amount ranging from 50% to 70% by weight relative to the total weight of the at least one block polymer.

23. The composition according to claim 1, wherein the block with a Tg of greater than or equal to 40° C. comprises at least one monomer whose homopolymer has a glass transition temperature of greater than or equal to 40° C.

24. The composition according to claim 23, wherein the block with a Tg of greater than or equal to 40° C. comprises at least one monomer whose homopolymer has a glass transition temperature ranging from 40 to 150° C.

25. The composition according to claim 23, wherein the block with a Tg of greater than or equal to 40° C. comprises at least one monomer whose homopolymer has a glass transition temperature of greater than or equal to 50° C.

26. The composition according to claim 25, wherein the block with a Tg of greater than or equal to 40° C. comprises at least one monomer whose homopolymer has a glass transition temperature ranging from 50° C. to 120° C.

27. The composition according to claim 25, wherein the block with a Tg of greater than or equal to 40° C. comprises at least one monomer whose homopolymer has a glass transition temperature of greater than or equal to 60° C.

28. The composition according to claim 27, wherein the block with a Tg of greater than or equal to 40° C. comprises at least one monomer whose homopolymer has a glass transition temperature ranging from 60° C. to 120° C.

29. The composition according to claim 23, wherein the block with a Tg of greater than or equal to 40° C. is a copolymer comprising monomers whose homopolymer has a glass transition temperature of greater than or equal to 40° C.

30. The composition according to claim 23, wherein the at least one monomer whose homopolymer has a glass transition temperature of greater than or equal to 40° C. is chosen from the following monomers:

methacrylates of formula $CH_2\!=\!C(CH_3)\!-\!COOR_1$
wherein $R_1$ is chosen from linear and branched unsubstituted alkyl groups comprising from 1 to 4 carbon atoms or $R_1$ is chosen from $C_4$ to $C_{12}$ cycloalkyl groups, acrylates of formula $CH_2\!=\!CH\!-\!COOR_2$
wherein $R_2$ is chosen from $C_4$ to $C_{12}$ cycloalkyl groups and a tert-butyl group, and (meth)acrylamides of formula:

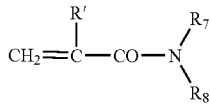

wherein $R_7$ and $R_8$, which may be identical or different, are each chosen from a hydrogen atom and linear and branched alkyl groups comprising from 1 to 12 carbon atoms; or $R_7$ is H and $R_8$ is a 1,1-dimethyl-3-oxobutyl group, and R' is chosen from H and methyl.

31. The composition according to claim 30, wherein $R_1$ is chosen from methyl, ethyl, propyl and isobutyl groups.

32. The composition according to claim 30, wherein $R_2$ is isobornyl acrylate.

33. The composition according to claim 30, wherein $R_7$ and $R_8$, which may be identical or different, are each chosen from n-butyl, t-butyl, isopropyl, isohexyl, isooctyl and isononyl groups.

34. The composition according to claim 23, wherein the at least one monomer whose homopolymer has a glass transition temperature of greater than or equal to 40° C. is chosen from methyl methacrylate, isobutyl methacrylate and isobornyl(meth)acrylate.

35. The composition according to claim 1, wherein the block with a Tg of greater than or equal to 40° C. is a homopolymer.

36. The composition according to claim 1, wherein the block with a Tg of less than or equal to 20° C. comprises at least one monomer whose homopolymer has a glass transition temperature of less than or equal to 20° C.

37. The composition according to claim 36, wherein the block with a Tg of less than or equal to 20° C. comprises at least one monomer whose homopolymer has a glass transition temperature ranging from −100 to 20° C.

38. The composition according to claim 36, wherein the block with a Tg of less than or equal to 20° C. comprises at least one monomer whose homopolymer has a glass transition temperature of less than or equal to 15° C.

39. The composition according to claim 38, wherein the block with a Tg of less than or equal to 20° C. comprises at least one monomer whose homopolymer has a glass transition temperature ranging from −80° C. to 15° C.

40. The composition according to claim 38, wherein the block with a Tg of less than or equal to 20° C. comprises at least one monomer whose homopolymer has a glass transition temperature of less than or equal to 10° C.

41. The composition according to claim 40, wherein the block with a Tg of less than or equal to 20° C. comprises at least one monomer whose homopolymer has a glass transition temperature ranging from −50° C. to 0° C.

42. The composition according to claim 36, wherein the at least one monomer whose homopolymer has a glass transition temperature of less than or equal to 20° C. is chosen from the following monomers:

acrylates of formula $CH_2\!=\!CHCOOR_3$,
wherein $R_3$ is chosen from linear and branched $C_1$ to $C_{12}$ unsubstituted alkyl groups, with the exception of the tert-butyl group, in which at least one hetero atom chosen from O, N and S is optionally intercalated;

methacrylates of formula $CH_2\!=\!C(CH_3)\!-\!COOR_4$,
wherein $R_4$ is chosen from linear and branched $C_6$ to $C_{12}$ unsubstituted alkyl groups, in which at least one hetero atom chosen from O, N and S is optionally intercalated;

vinyl esters of formula $R_5\!-\!CO\!-\!O\!-\!CH\!=\!CH_2$
wherein $R_5$ is chosen from linear and branched $C_4$ to $C_{12}$ alkyl groups, $C_4$ to $C_{12}$ alkyl vinyl ethers; and N—($C_4$ to $C_{12}$)alkyl acrylamides.

43. The composition according to claim 42, wherein the $C_4$ to $C_{12}$ alkyl vinyl ethers are chosen from methyl vinyl ether and ethyl vinyl ether.

44. The composition according to claim 42, wherein the N—($C_4$ to $C_{12}$)alkyl acrylamide is N-octylacrylamide.

45. The composition according to claim 36, wherein the at least one monomer whose homopolymer has a glass transition temperature of less than or equal to 20° C. is chosen from alkyl acrylates whose alkyl chain comprises from 1 to 10 carbon atoms, with the exception of the tert-butyl group.

46. The composition according to claim 1, wherein the block with a glass transition temperature of less than or equal to 20° C. is a homopolymer.

47. The composition according to claim 1, wherein the block with a Tg of between 20 and 40° C. comprises at least one monomer whose homopolymer has a glass transition temperature of between 20 and 40° C.

48. The composition according to claim 1, wherein the block with a Tg of between 20 and 40° C. is a homopolymer of a monomer chosen from n-butyl methacrylate, cyclodecyl acrylate, neopentyl acrylate and isodecylacrylamide.

49. The composition according to claim 1, wherein the block with a Tg of between 20 and 40° C. is a copolymer comprising:
at least one monomer whose homopolymer has a Tg of greater than or equal to 40° C., and
at least one monomer whose homopolymer has a Tg of less than or equal to 20° C.

50. The composition according to claim 1, wherein the block with a Tg of between 20 and 40° comprises at least one monomer chosen from methyl methacrylate, isobornyl(meth)acrylate, trifluoroethyl methacrylate, butyl acrylate and 2-ethylhexyl acrylate.

51. The composition according to claim 1, wherein at least one of the first block and the second block comprises at least one additional monomer.

52. The composition according to claim 51, wherein the at least one additional monomer is chosen from hydrophilic monomers and monomers comprising at least one ethylenic unsaturation comprising at least one silicon atom.

53. The composition according to claim 51, wherein the at least one additional monomer is chosen from:

ethylenically unsaturated monomers comprising at least one functional group chosen from carboxylic and sulfonic acid functional groups, methacrylates of formula $CH_2=C(CH_3)-COOR_6$ wherein $R_6$ is an alkyl group chosen from linear and branched alkyl groups comprising from 1 to 4 carbon atoms, wherein said alkyl group is substituted with at least one substituent chosen from hydroxyl groups and halogen atoms, methacrylates of formula $CH_2=C(CH_3)-COOR_9$, wherein $R_9$ is an alkyl group chosen from linear and branched $C_6$ to $C_{12}$ alkyl groups in which at least one hetero atom chosen from O, N and S is optionally intercalated, wherein said alkyl group is substituted with at least one substituent chosen from hydroxyl groups and halogen atoms;

acrylates of formula $CH_2=CHCOOR_{10}$, wherein $R_{10}$ is chosen from linear and branched $C_1$ to $C_{12}$ alkyl groups substituted with at least one substituent chosen from hydroxyl groups and halogen atoms, or $R_{10}$ is chosen from $C_1$ to $C_{12}$ alkyl-O-POE (polyoxyethylene) with repetition of the oxyethylene unit from 5 to 30 times, or $R_{10}$ is chosen from polyoxyethylenated groups comprising from 5 to 30 ethylene oxide units; and ethylenically unsaturated monomers comprising at least one tertiary amine functional group.

54. The composition according to claim 51, wherein the at least one additional monomer is chosen from acrylic acid, methacrylic acid and trifluoroethyl methacrylate.

55. The composition according to claim 51, wherein the at least one additional monomer is present in an amount ranging from 1% to 30% by weight relative to the total weight of the at least one of the first block and the second block.

56. The composition according to claim 1, wherein each of the first and second blocks comprises at least one monomer chosen from (meth)acrylic acid esters, and optionally at least one monomer chosen from (meth)acrylic acids.

57. The composition according to claim 1, wherein each of the first and second blocks consists of at least one monomer chosen from (meth)acrylic acid esters, and optionally at least one monomer chosen from (meth)acrylic acids.

58. The composition according to claim 1, wherein the first and second blocks are such that the difference between the glass transition temperatures (Tg) of the first and second blocks is greater than 10° C.

59. The composition according to claim 58, wherein the first and second blocks are such that the difference between the glass transition temperatures (Tg) of the first and second blocks is greater than 20° C.

60. The composition according to claim 59, wherein the first and second blocks are such that the difference between the glass transition temperatures (Tg) of the first and second blocks is greater than 30° C.

61. The composition according to claim 60, wherein the first and second blocks are such that the difference between the glass transition temperatures (Tg) of the first and second blocks is greater than 40° C.

62. The composition according to claim 1, wherein the intermediate block has a glass transition temperature that is between the glass transition temperatures of the first and second blocks.

63. The composition according to claim 1, wherein the at least one block polymer has a polydispersity index I of greater than or equal to 2.8.

64. The composition according to claim 63, wherein the at least one block polymer has a polydispersity index I ranging from 2.8 to 6.

65. The composition according to claim 1, wherein the at least one block polymer has a weight-average molecular weight (Mw) of less than or equal to 300 000.

66. The composition according to claim 65, wherein the at least one block polymer has a weight-average molecular weight (Mw) ranging from 35 000 to 200 000.

67. The composition according to claim 66, wherein the at least one block polymer has a weight-average molecular weight (Mw) ranging from 45 000 to 150 000.

68. The composition according to claim 1, wherein the at least one block polymer has a number-average molecular weight (Mn) of less than or equal to 70 000.

69. The composition according to claim 68, wherein the at least one block polymer has a number-average molecular weight (Mn) ranging from 10 000 to 60 000.

70. The composition according to claim 69, wherein the at least one block polymer has a number-average molecular weight (Mn) ranging from 12 000 to 50 000.

71. The composition according to claim 1, wherein the at least one block polymer is not soluble at an active material content of at least 1% by weight in water or in a mixture of water and at least one monoalcohol chosen from linear and branched lower monoalcohols comprising from 2 to 5 carbon atoms, without pH modification, at room temperature (25° C.).

72. The composition according to claim 1, wherein the at least one block polymer is present in an amount ranging from 0.1% to 90% by weight, relative to the total weight of the composition.

73. The composition according to claim 72, wherein the at least one block polymer is present in an amount ranging from 0.5% to 50% by weight, relative to the total weight of the composition.

74. The composition according to claim 73, wherein the at least one block polymer is present in an amount ranging from 0.5% to 30% by weight, relative to the total weight of the composition.

75. The composition according to claim 1, wherein the at least one non-volatile silicone oil is chosen from non-volatile polydimethylsiloxanes (PDMSs); polydimethylsiloxanes comprising at least one group chosen from alkyl, alkoxy and phenyl groups, pendent or at the end of a silicone chain, wherein the at least one group comprises from 2 to 24 carbon atoms; phenyl silicones; polysiloxanes modified with at least one entity chosen from fatty acids, fatty alcohols and polyoxyalkylenes; amino silicones; silicones comprising at least one hydroxyl group; and fluoro silicones comprising at least one fluoro group that is pendent or at the end of a silicone chain, comprising from 1 to 12 carbon atoms, at least one of the hydrogens of which is replaced with a fluorine atom.

76. The composition according to claim 75, wherein the fatty acids are chosen from $C_8$-$C_{20}$ fatty acids.

77. The composition according to claim 75, wherein the fatty alcohols are chosen from $C_8$-$C_{20}$ fatty alcohols.

78. The composition according to claim 75, wherein the polyoxyalkylenes are chosen from polyoxyethylene and polyoxypropylene.

79. The composition according to claim 1, wherein the at least one non-volatile silicone oil is chosen from non-volatile phenyl silicone oils.

80. The composition according to claim 79, wherein the non-volatile phenyl silicone oils are chosen from phenyl trimethicones, phenyl dimethicones, phenyltrimethylsiloxydiphenylsiloxanes, diphenyl dimethicones and diphenylmethyldiphenyltrisiloxanes, and mixtures thereof.

81. The composition according to claim 79, wherein the non-volatile phenyl silicone oils are chosen from the phenyl silicones of formula (VI) below:

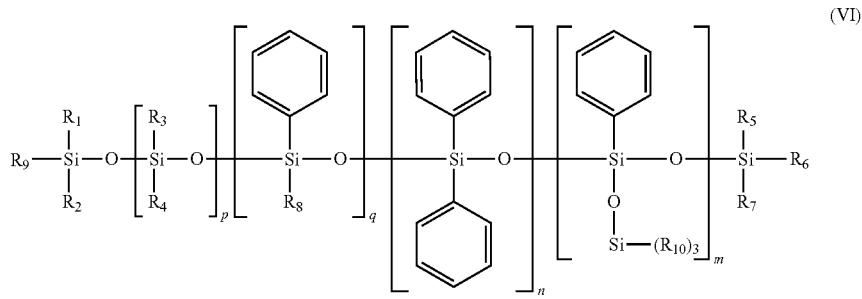

wherein
R1 to R10, which may be identical or different, are each chosen from saturated and unsaturated, linear, cyclic and branched $C_1$-$C_{30}$ hydrocarbon-based radicals, and
m, n, p and q, which may be identical or different, are each chosen from integers ranging from 0 to 900, with the proviso that the sum "m+n+q" is other than 0.

82. The composition according to claim 81, wherein:
the sum "m+n+q" ranges from 1 to 100,
the sum "m+n+p+q" ranges from 1 to 900, or
q is equal to 0.

83. The composition according to claim 82, wherein the sum "m+n+p+q" ranges from 1 to 800.

84. The composition according to claim 81, wherein the phenyl silicone oil of formula (VI) has a viscosity at 25° C. ranging from 5 to 1500 mm$^2$/s.

85. The composition according to claim 84, wherein the phenyl silicone oil of formula (VI) has a viscosity at 25° C. ranging from 5 to 1000 mm$^2$/s.

86. The composition according to claim 79, wherein the non-volatile phenyl silicone oil is chosen from the phenyl silicones of formula (VII) below:

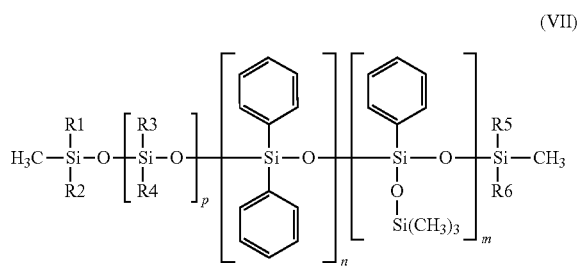

wherein:
R1 to R6, which may be identical or different, are each chosen from saturated and unsaturated, linear, cyclic and branched $C_1$-$C_{30}$ hydrocarbon-based radicals, and
m, n and p, which may be identical or different, are each chosen from integers ranging from 0 to 100, with the proviso that the sum "n+m" ranges from 1 to 100.

87. The composition according to claim 86, wherein R1 to R6, which may be identical or different, are each chosen from linear and branched, saturated $C_1$-$C_{30}$ and hydrocarbon-based radicals.

88. The composition according to claim 87, wherein R1 to R6, which may be identical or different, are each chosen from linear and branched, saturated $C_1$-$C_{12}$ and hydrocarbon-based radicals.

89. The composition according to claim 88, wherein R1 to R6, which may be identical or different, are each chosen from methyl, ethyl, propyl and butyl radicals.

90. The composition according to claim 86, wherein R1 to R6 are identical and are each a methyl radical.

91. The composition according to claim 86, wherein m=1, 2 or 3, and/or n=0 and/or p=0 or 1.

92. The composition according to claim 86, wherein the phenyl silicone oil has a weight-average molecular weight ranging from 500 to 10 000.

93. The composition according to claim 1, wherein the at least one non-volatile silicone oil is present in an amount ranging from 30% to 95% by weight, relative to the total weight of the non-volatile liquid fatty phase.

94. The composition according to claim 93, wherein the at least one non-volatile silicone oil is present in an amount ranging from 40% to 85% by weight, relative to the total weight of the non-volatile liquid fatty phase.

95. The composition according to claim 94, wherein the at least one non-volatile silicone oil is present in an amount ranging from 50% to 80% by weight, relative to the total weight of the non-volatile liquid fatty phase.

96. The composition according to claim 1, wherein the at least one non-volatile silicone oil is present in an amount ranging from 0.1% to 70% by weight, relative to the total weight of the composition.

97. The composition according to claim 96, wherein the at least one non-volatile silicone oil is present in an amount ranging from 1% to 50% by weight, relative to the total weight of the composition.

98. The composition according to claim 97, wherein the at least one non-volatile silicone oil is present in an amount ranging from 1% to 30% by weight, relative to the total weight of the composition.

99. The composition according to claim 1, further comprising at least one non-silicone non-volatile oil.

100. The composition according to claim 99, wherein the at least one non-silicone non-volatile oil is chosen from liquid paraffin, squalane, hydrogenated polyisobutylene, perhydrosqualene, mink oil, turtle oil, soybean oil, sweet almond oil, beauty-leaf oil, palm oil, grape seed oil, sesame seed oil, maize oil, arara oil, rapeseed oil, sunflower oil, cotton seed oil, apricot oil, castor oil, avocado oil, jojoba oil, olive oil or cereal germ oil; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate and lactate, bis(2-ethylhexyl)succinate, diisostearyl malate, glyceryl and diglyceryl triisostearates, myristic acid, palmitic acid, stearic acid, behenic acid, oleic acid, linoleic acid, linolenic acid and isostearic acid; and $C_{16}$-$C_{22}$ fatty alcohols.

101. The composition according to claim 99, wherein the at least one non-silicone non-volatile oil is present in an amount ranging from 0.1% to 70% by weight, relative to the total weight of the non-volatile liquid fatty phase.

102. The composition according to claim 101, wherein the at least one non-silicone non-volatile oil is present in an amount ranging from 0.1% to 60% by weight, relative to the total weight of the composition.

103. The composition according to claim 1, further comprising at least one volatile oil.

104. The composition according to claim 103, wherein the at least one volatile oil is chosen from octamethylcyclotetrasiloxane, decamethylcyclopentasiloxane, dodecamethylcyclohexasiloxane, heptamethyl-hexyltrisiloxane, heptamethyloctyltrisiloxane, octamethyltrisiloxane, decamethyltetrasiloxane, isododecane, isodecane and isohexadecane.

105. The composition according to claim 103, wherein the at least one volatile oil is present in an amount ranging from 0.1% to 90% by weight, relative to the total weight of the composition.

106. The composition according to claim 1, further comprising at least one fatty substance that is solid at room temperature, chosen from waxes, pasty fatty substances and gums.

107. The composition according to claim 106, wherein the waxes are present in an amount ranging from 0.1% to 50% by weight, relative to the total weight of the composition.

108. The composition according to claim 1, further comprising at least one dyestuff.

109. The composition according to claim 108, further comprising at least one cosmetic ingredient chosen from additional film-forming polymers, vitamins, thickeners, trace elements, softeners, sequestering agents, fragrances, acidifying and basifying agents, preserving agents, sunscreens, surfactants, antioxidants, agents for preventing hair loss, antidandruff agents and propellants.

110. The composition according to claim 1, wherein the composition is in a form chosen from a suspension, a dispersion, a solution, a gel, an emulsion, a cream, a paste, a mousse, a vesicular dispersion, a two-phase lotion, a multi-phase lotion, a spray and a stick.

111. The composition according to claim 110, wherein the emulsion is chosen from oil-in-water (O/W), water-in-oil (W/O) and multiple (W/O/W and polyol/O/W and O/W/O) emulsions.

112. The composition according to claim 110, wherein the vesicular dispersion is chosen from vesicular dispersions of ionic and nonionic lipids.

113. The composition according to claim 1, wherein the composition is in anhydrous form.

114. A composition for making up and/or caring for a keratin material, comprising at least one block polymer and a cosmetically acceptable organic liquid medium comprising a non-volatile liquid fatty phase, wherein:
the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:
a) a block with a Tg of greater than or equal to 40° C.,
b) a block with a Tg of less than or equal to 20° C.,
c) a block with a Tg of between 20 and 40° C., and
the at least one second block is chosen from a category a), b) or c) different from the at least one first block,
the non-volatile liquid fatty phase comprises at least 30% by weight of at least one non-volatile silicone oil, relative to the total weight of the non-volatile liquid fatty phase, and
the at least one block polymer is non-elastomeric.

115. A lip makeup product, comprising at least one block polymer and a cosmetically acceptable organic liquid medium comprising a non-volatile liquid fatty phase, wherein:
the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:
a) a block with a Tg of greater than or equal to 40° C.,
b) a block with a Tg of less than or equal to 20° C.,
c) a block with a Tg of between 20 and 40° C., and
the at least one second block is chosen from a category a), b) or c) different from the at least one first block,
the non-volatile liquid fatty phase comprises at least 30% by weight of at least one non-volatile silicone oil, relative to the total weight of the non-volatile liquid fatty phase, and
the at least one block polymer is non-elastomeric.

116. A cosmetic assembly comprising:
a) a container delimiting at least one compartment, wherein said container is closed by a closing member; and
b) a composition placed inside said at least one compartment, wherein the composition comprises at least one block polymer and a cosmetically acceptable organic liquid medium comprising a non-volatile liquid fatty phase, wherein:
the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:
a) a block with a Tg of greater than or equal to 40° C.,
b) a block with a Tg of less than or equal to 20° C.,
c) a block with a Tg of between 20 and 40° C., and the at least one second block is chosen from a category a), b) or c) different from the at least one first block, the non-volatile liquid fatty phase comprises at least 30% by weight of at least one non-volatile silicone oil, relative to the total weight of the non-volatile liquid fatty phase, and the at least one block polymer is non-elastomeric.

117. The cosmetic assembly according to claim 116, wherein the container is at least partially formed from at least one thermoplastic material.

118. The cosmetic assembly according to claim 116, wherein the container is at least partially formed from at least one non-thermoplastic material.

119. The cosmetic assembly according to claim 118, wherein the container is at least partially formed from at least one of glass and metal.

120. The cosmetic assembly according to claim 116, wherein, in the closed position of the container, the closing member is screwed onto the container.

121. The cosmetic assembly according to claim 116, wherein, in the closed position of the container, the closing member is coupled to the container other than by screwing.

122. The cosmetic assembly according to claim 121, wherein, in the closed position of the container, the closing member is coupled to the container by click-fastening, bonding or welding.

123. The cosmetic assembly according to claim 116, wherein the composition is substantially at atmospheric pressure inside the compartment.

124. The cosmetic assembly according to claim 116, wherein the composition is pressurized inside the container.

125. A cosmetic process for making up and/or caring for a keratin material, comprising applying to the keratin material a cosmetic composition comprising at least one block polymer and a cosmetically acceptable organic liquid medium comprising a non-volatile liquid fatty phase, wherein:

the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:

a) a block with a Tg of greater than or equal to 40° C.,
b) a block with a Tg of less than or equal to 20° C.,
c) a block with a Tg of between 20 and 40° C., and the at least one second block is chosen from a category a), b) or c) different from the at least one first block, the non-volatile liquid fatty phase comprises at least 30% by weight of at least one non-volatile silicone oil, relative to the total weight of the non-volatile liquid fatty phase, and the at least one block polymer is non-elastomeric.

126. A method for obtaining a deposit on a keratin material, which has transfer-resistance properties and is comfortable over time, comprising applying to the keratin material a composition, comprising at least one block polymer and a cosmetically acceptable organic liquid medium comprising a non-volatile liquid fatty phase, wherein:

the at least one block polymer is chosen from film-forming linear ethylenic polymers, has a polydispersity index of greater than or equal to 2.5, and comprises at least one first block and at least one second block with different glass transition temperatures (Tg) connected together via an intermediate block comprising at least one constituent monomer of the at least one first block and at least one constituent monomer of the at least one second block, wherein the at least one constituent monomer of the at least one first block differs from the at least one constituent monomer of the at least one second block, said intermediate block is a random copolymer block, and the at least one first block of the polymer is chosen from:

a) a block with a Tg of greater than or equal to 40° C.,
b) a block with a Tg of less than or equal to 20° C.,
c) a block with a Tg of between 20 and 40° C., and the at least one second block is chosen from a category a), b) or c) different from the at least one first block, the non-volatile liquid fatty phase comprises at least 30% by weight of at least one non-volatile silicone oil, relative to the total weight of the non-volatile liquid fatty phase, and the at least one block polymer is non-elastomeric.

127. The method according to claim 126, wherein the keratin material is chosen from skin and lips.

* * * * *